US005856095A

United States Patent [19]
Evans et al.

[11] Patent Number: 5,856,095
[45] Date of Patent: Jan. 5, 1999

[54] IDENTIFICATION OF TWO NOVEL MUTANT ALLELES OF HUMAN THIOPURINE S-METHYLTRANSFERASE, AND DIAGNOSTIC USES THEREOF

[75] Inventors: William E. Evans; Eugene Y. Krynetski, both of Cordova, Tenn.

[73] Assignee: St. Jude Children's Research Hospital, Memphis, Tenn.

[21] Appl. No.: 514,921

[22] Filed: Aug. 14, 1995

[51] Int. Cl.$^6$ .............................. C12Q 1/68; C12P 19/34; C07H 21/04

[52] U.S. Cl. .............................. 435/6; 435/912; 435/810; 536/24.31; 536/24.33; 536/23.5; 935/8; 935/9; 935/78

[58] Field of Search .............................. 435/6, 912, 810; 536/24.33, 23.5; 935/8, 9, 78

[56] References Cited

U.S. PATENT DOCUMENTS 5,470,737  11/1995  Weinshilboum ..................... 435/240.2

OTHER PUBLICATIONS

The Bochringer Mahnheim Catalog (1989) p. 144.
Chomczynski, P., and Sacchi, N., "Single–Step Method of RNA Isolation by Acid Guanidinium Thiocyanate–Phenol–Chloroform Extraction," *Analyt. Biochem.* 162:156–159 (1987).
Ciechanover, A., and Schwartz, A.L., "The Ubiquitin–Mediated Proteolytic Pathway: Mechanisms of Recognition of the Proteolytic Substrate and Involvement in the Degradation of Native Cellular Proteins," *FASEB J.* 8:182–191 (Feb. 1994).
Evans, W.E., et al., "Altered Mercaptopurine Metabolism, Toxic Effects, and Dosage Requirement in a Thiopurine Methyltransferase–Deficient Child with Acute Lymphocytic Leukemia," *J. Pediatr.* 119(6):985–989 (1991).
Grant, D.M., "Molecular Genetics of the N–Acetyltransferases," *Pharmacogenetics* 3:45–50 (1993).
Heim, M., and Meyer, U.A., "Genotyping of Poor Metabolisers of Debrisoquine by Allele–Specific PCR Amplification," *Lancet* 336:529–532 (1990).
Hollander, A.A.M.J., et al., "Beneficial Effects of Conversion from Cyclosporin to Azathioprine After Kidney Transplantation," *Lancet* 345:610–614 (Mar. 11, 1995).
Honchel, R., et al., "Human Thiopurine Methyltransferase: Molecular Cloning and Expression of T84 Colon Carcinoma Cell cDNA," *Molec. Pharmacol* 43:878–887 (1993).
Jin. A., et al., "New Restriction Endonuclease CviRI Cleaves DNA at TG/CA Sequences," *Nucl. Acids Res.* 22(19):3928–3929 (Sep. 25, 1994).
Köhler, G., and Milstein, C., "Continuous Cultures of Fused Cells Secreting Antibody of Predefined Specificity," *Nature* 256:495–497 (1975).
Krynetski, E.Y., et al., "A Single Point Mutation Leading to Loss of Catalytic Activity in Human Thiopurine S–methyltransferase," *Proc. Natl. Acad. Sci. USA* 92:949–953 (Feb. 1995).
Krynetski, E.Y., et al., "High Yield Expression of Functionally Active Human Liver CYP2D6 in Yeast Cells," *Pharmacogenetics* 5(2):103–109 (Apr. 1995).

(List continued on next page.)

*Primary Examiner*—Carla J. Myers
*Attorney, Agent, or Firm*—Sterne, Kessler, Goldstein & Fox, PLLC

[57] ABSTRACT

Mutants of thiopurine S-methyltransferase (TPMT) are described. TPMTA mutant has a point mutation at cDNA position 238 ($G^{238} \to C$), and TPMTB involves two nucleotide transitions at cDNA positions 460 ($G^{460} \to A$) and 719 ($A^{719} \to G$). TPMTB is the predominant mutant allele associated with human TPMT-deficiency which can cause potentially fatal toxicity when patients are treated with mercaptopurine, azathioprine, or thioguanine. The mutant alleles as well as PCR fragments, mutant proteins and antibodies therefor, together with kits and methods for assaying the TPMT genotype of individual patients are disclosed.

22 Claims, 21 Drawing Sheets

OTHER PUBLICATIONS

Krynetski, E.Y., et al., "Methylation of Mercaptopurine, Thioguanine, and Their Nucleotide Metabolites by Heterologously Expressed Human Thiopurine S–Methyltransferase," *Mol. Pharmacol.* 47:1141–1147 (Jun. 1995).

Krynetsky, E.Yu., et al., "Effects of Amino–Terminus Truncation in Human Cytochrome P450IID6 on Ints Insertion Into the Endoplasmic Reticulum Membrane of *Saccharomyces cerevisiae*," *FEBS Lett.* 336(1):87–89 (1993).

Lee, D., et al., "Thiopurine Methyltransferase Pharmacogenetics. Cloning of Human Liver cDNA and a Processed Pseudogene on Human Chromosome 18q21.1," *Drug Metab. Disp.* 23(3):398–405 (Mar. 1995).

Lennard, L., et al., "Thiopurine Pharmacogenetics in Leukemia: Correlation of Erythrocyte Thiopurine Methyltransferase Activity and 6–Thioguanine Nucleotide Concentrations," *Clin. Pharmacol. Ther.* 41(1):18–25 (1987).

Lennard, L., et al., "Congenital Thiopurine Methyltransferase Deficiency and 6–Mercaptopurine Toxicity During Treatment for Acute Lymphoblastic Leukemia," *Arch. Dis. Child.* 69:577–579 (1993).

McLeod, H.L., et al., "Azathioprine–Induced Myelosuppression in Thiopurine Methyltransferase Deficient Heart Transplant Recipient," *Lancet 341*:1151 (1993).

McLeod, H.L., et al., "Higher Activity of Polymorphic Thiopurine S–Methyltransferase in Erythrocytes From Neonates Compared to Adults," *Pharmacogenetics 5(5)*:281–286 (Jul. 1995).

Pacifici, G.M., et al., "S–Methyltransferases in Human Intestine: Differential Distribution of the Microsomal Thiol Methyltransferase and Cytosolic Thiopurine Methyltransferase Along the Human Bowel," *Xenobiotica 23*:671–679 (1993).

Purmal, A.A., et al., "5–Hydroxypyrimidine Deoxynucleoside Triphosphates are More Efficiently Incorporated into DNA by Exonuclease–Free Klenow Fragment than 8–Oxopurine Deoxynucleoside Triphosphates," *Nucl. Acids. Res.* 22(19):3930–3935 (Sep. 25, 1994).

Schmitt, M.E., et al., "A Rapid and Simple Method For Preparation of RNA From *Saccharomyces cerevisiae*," *Nucl. Acids Res. 18(10)*:3091–3092 (1990).

Schütz, E., et al., "Azathioprine–Induced Myelosuppression in Thiopurine Methyltransferase Deficient Heart Transplant Recipient," *Lancet 341:*436 (1993).

Siebert, P.D., et al., "An Improved PCR Method for Walking in Uncloned Genomic DNA," *Nucl. Acids Res. 23(6):*1087–1088 (Mar. 1995).

Van Loon, J.A., and Weinshilboum, R.M., "Thiopurine Methyltransferaes Isozymes in Human Renal Tissue," *Drug Metab. Dispos.* 18(5):632–638 (1990).

Van Loon, J.A., et al., "Human Kidney Thiopurine Methyltransferase. Photoaffinity Labeling with S–Adenosyl–L–Methionine," *Biochem. Pharmacol.* 44(4):775–785 (1992).

Weinshilboum, R.M., et al., "Human Erythrocyte Thiopurine Methyltransferase: Radiochemical Microassay and Biochemical Properties," *Clin. Chim. Acta 85:*323–333 (1978).

Weinshilboum, R.M., and Sladek, S.L., "Mercaptopurine Pharmacogenetics: Monogenic Inheritance of Erythrocyte Thiopurine Methyltransferase Activity," *Am. J. Human Genet.* 32:651–662 (1980).

Woodson, L.C., et al., "Pharmacogenetics of Human Thiopurine Methyltransferase: Kidney–Erythrocyte Correlation and Immuntitration Studies," *J. Pharmacol. Exp. Ther. 222(1):*174–181 (1982).

1 2 3

1 2 3 M 1 2 3

1 2 3 M

```
CGGCAACCAGCTGTAAGCGAGGCACGGAAGACATATGCTTGTGAGACAAAGGTGTCTCTG    -6
     1
AAACTATGGATGGTACAAGAACTTCACTTGACATTGAAGAGTACTCGGATACTGAGGTAC    55
    M  D  G  T  R  T  S  L  D  I  E  E  Y  S  D  T  E  V  Q

AGAAAAACCAAGTACTAACTCTGGAAGAATGGCAAGACAAGTGGGTGAACGGCAAGACTG    115
 K  N  Q  V  L  T  E  E  W  Q  D  K  W  V  N  G  K  T  A

CTTTTCATCAGGAACAAGGACATCAGCTATTAAAGAAGCATTTAGATACTTTCCTTAAAG    175
 F  H  Q  E  Q  G  H  Q  L  L  K  K  H  L  D  T  F  L  K  G

GCAAGAGTGGACTGAGGGTATTTTTTCCTCTTTGCGGAAAAGCGGTTGAGATGAAATGGT    235
 K  S  G  L  R  V  F  F  P  L  C  G  K  A  V  E  M  K  W  F

TTCCAGACCGGGGACACAGTGTAGTTGGTGTGGAAATCAGTGAACTTGGGATACAAGAAT    295
 P  D  R  G  H  S  V  V  G  V  E  I  S  E  L  G  I  Q  E  F

TTTTTACAGAGCAGAATCTTTCTTACTCAGAAGAACCAATCACCGAAATTCCTGGAACCA    355
 F  T  E  Q  N  L  S  Y  S  E  E  P  I  T  E  I  P  G  T  K

AAGTATTTAAGAGTTCTTCGGGGAACATTTCATTGTACTGTTGCAGTATTTTTGATCTTC    415
 V  F  K  S  S  S  G  N  I  S  L  Y  C  C  S  I  F  D  L  P

CCAGGACAAATATTGGCAAATTTGACATGATTTGGGATAGAGGAGCATTAGTTGCCATTA    475
 R  T  N  I  G  K  F  D  M  I  W  D  R  G  A  L  V  A  I  N

ATCCAGGTGATCGCAAATGCTATGCAGATACAATGTTTTCCCTCCTGGGAAAGAAGTTTC    535
 P  G  D  R  K  C  Y  A  D  T  M  F  S  L  L  G  K  K  F  Q

AGTATCTCCTGTGTGTTCTTTCTTATGATCCAACTAAACATCCAGGTCCACCATTTTATG    595
 Y  L  L  C  V  L  S  Y  D  P  T  K  H  P  G  P  P  F  Y  V
```

FIG. 11A

TTCCACATGCTGAAATTGAAAGGTTGTTTGGTAAAATATGCAATATACGTTGTCTTGAGA    655
 P  H  A  E  I  E  R  L  F  G  K  I  C  N  I  R  C  L  E  K

AGGTTGATGCTTTTGAAGAACGACATAAAAGTTGGGGAATTGACTGTCTTTTTGAAAAGT    715
 V  D  A  F  E  E  R  H  K  S  W  G  I  D  C  L  F  E  K  L

TATATCTACTTACAGAAAAGTAAATGAGACATAGATAAAATAAAATCACACTGACATGTT    775
 Y  L  L  T  E  K  *

FIG. 11B

CGGCAACCAGCTGTAAGCGAGGCACGGAAGACATATGCTTGTGAGACAAAGGTGTCTCTG     -6

```
                                                                                  1
AAACTATGGATGGTACAAGAACTTCACTTGACATTGAAGAGTACTCGGATACTGAGGTAC    55
      M  D  G  T  R  T  S  L  D  I  E  E  Y  S  D  T  E  V  Q
AGAAAAACCAAGTACTAACTCTGGAAGAATGGCAAGACAAGTGGGTGAACGGCAAGACTG   115
  K  N  Q  V  L  T  L  E  E  W  Q  D  K  W  V  N  G  K  T  A
CTTTTCATCAGGAACAAGGACATCAGCTATTAAAGAAGCATTTAGATACTTTCCTTAAAG   175
  F  H  Q  E  Q  G  H  Q  L  L  K  K  H  L  D  T  F  L  K  G
GCAAGAGTGGACTGAGGGTATTTTTTCCTCTTTGCGGAAAAGCGGTTGAGATGAAATGGT   235
  K  S  G  L  R  V  F  F  P  L  C  G  K  A  V  E  M  K  W  F
TTGCAGACCGGGGACACAGTGTAGTTGGTGTGGAAATCAGTGAACTTGGGATACAAGAAT   295
  A  D  R  G  H  S  V  V  G  V  E  I  S  E  L  G  I  Q  E  F
TTTTTACAGAGCAGAATCTTTCTTACTCAGAAGAACCAATCACCGAAATTCCTGGAACCA   355
  F  T  E  Q  N  L  S  Y  S  E  E  P  I  T  E  I  P  G  T  K
AAGTATTTAAGAGTTCTTCGGGGAACATTTCATTGTACTGTTGCAGTATTTTTGATCTTC   415
  V  F  K  S  S  S  G  N  I  S  L  Y  C  C  S  I  F  D  L  P
CCAGGACAAATATTGGCAAATTTGACATGATTTGGGATAGAGGAACATTAGTTGCCATTA   475
  R  T  N  I  G  K  F  D  M  I  W  D  R  G  T  L  V  A  I  N
ATCCAGGTGATCGCAAATGCTATGCAGATACAATGTTTTCCCTCCTGGGAAAGAAGTTTC   535
  P  G  D  R  K  C  Y  A  D  T  M  F  S  L  L  G  K  K  F  Q
```

FIG. 12A

```
AGTATCTCCTGTGTGTTCTTTCTTATGATCCAACTAAACATCCAGGTCCACCATTTTATG    595
  Y  L  L  C  V  L  S  Y  D  P  T  K  H  P  G  P  P  F  Y  V

TTCCACATGCTGAAATTGAAAGGTTGTTTGGTAAAATATGCAATATACGTTGTCTTGAGA    655
  P  H  A  E  I  E  R  L  F  G  K  I  C  N  I  R  C  L  E  K

AGGTTGATGCTTTTGAAGAACGACATAAAAGTTGGGGAATTGACTGTCTTTTTGAAAAGT    715
  V  D  A  F  E  E  R  H  K  S  W  G  I  D  C  L  F  E  K  L

TATATCTACTTACAGAAAAGTAAATGAGACATAGATAAAATAAAATCACACTGACATGTT    775
  Y  L  L  T  E  K  *
```

FIG. 12B

```
CGGCAACCAGCTGTAAGCGAGGCACGGAAGACATATGCTTGTGAGACAAAGGTGTCTCTG    -6

1
AAACTATGGATGGTACAAGAACTTCACTTGACATTGAAGAGTACTCGGATACTGAGGTAC    55
      M  D  G  T  R  T  S  L  D  I  E  E  Y  S  D  T  E  V  Q

AGAAAAACCAAGTACTAACTCTGGAAGAATGGCAAGACAAGTGGGTGAACGGCAAGACTG    115
   K  N  Q  V  L  T  L  E  E  W  Q  D  K  W  V  N  G  K  T  A

CTTTTCATCAGGAACAAGGACATCAGCTATTAAAGAAGCATTTAGATACTTTCCTTAAAG    175
   F  H  Q  E  Q  G  H  Q  L  L  K  K  H  L  D  T  F  L  K  G

GCAAGAGTGGACTGAGGGTATTTTTTCCTCTTTGCGGAAAAGCGGTTGAGATGAAATGGT    235
   K  S  G  L  R  V  F  F  P  L  C  G  K  A  V  E  M  K  W  F

TTGCAGACCGGGGACACAGTGTAGTTGGTGTGGAAATCAGTGAACTTGGGATACAAGAAT    295
   A  D  R  G  H  S  V  V  G  V  E  I  S  E  L  G  I  Q  E  F

TTTTTACAGAGCAGAATCTTTCTTACTCAGAAGAACCAATCACCGAAATTCCTGGAACCA    355
   F  T  E  Q  N  L  S  Y  S  E  E  P  I  T  E  I  P  G  T  K

AAGTATTTAAGAGTTCTTCGGGGAACATTTCATTGTACTGTTGCAGTATTTTTGATCTTC    415
   V  F  K  S  S  S  G  N  I  S  L  Y  C  C  S  I  F  D  L  P

CCAGGACAAATATTGGCAAATTTGACATGATTTGGGATAGAGGAGCATTAGTTGCCATTA    475
   R  T  N  I  G  K  F  D  M  I  W  D  R  G  A  L  V  A  I  N

ATCCAGGTGATCGCAAATGCTATGCAGATACAATGTTTTCCCTCCTGGGAAAGAAGTTTC    535
   P  G  D  R  K  C  Y  A  D  T  M  F  S  L  L  G  K  K  F  Q
```

FIG. 13A

```
AGTATCTCCTGTGTGTTCTTTCTTATGATCCAACTAAACATCCAGGTCCACCATTTTATG    595
   Y L L   C  V  L  S  Y  D  P  T  K  H  P  G  P  P  F  Y  V
TTCCACATGCTGAAATTGAAAGGTTGTTTGGTAAAATATGCAATATACGTTGTCTTGAGA    655
   P  H  A  E  I  E  R  L  F  G  K  I  C  N  I  R  C  L  E  K
AGGTTGATGCTTTTGAAGAACGACATAAAAGTTGGGGAATTGACTGTCTTTTTGAAAAGT    715
   V  D  A  F  E  E  R  H  K  S  W  G  I  D  C  L  F  E  K  L
TATGTCTACTTACAGAAAAGTAAATGAGACATAGATAAAATAAAATCACACTGACATGTT    775
   C  L  L  T  E  K  *
```

FIG. 13B

```
CGGCAACCAGCTGTAAGCGAGGCACGGAAGACATATGCTTGTGAGACAAAGGTGTCTCTG    -6

1
AAACTATGGATGGTACAAGAACTTCACTTGACATTGAAGAGTACTCGGATACTGAGGTAC    55
    M  D  G  T  R  T  S  L  D  I  E  E  Y  S  D  T  E  V  Q

AGAAAAACCAAGTACTAACTCTGGAAGAATGGCAAGACAAGTGGGTGAACGGCAAGACTG   115
  K  N  Q  V  L  T  L  E  E  W  Q  D  K  W  V  N  G  K  T

CTTTTCATCAGGAACAAGGACATCAGCTATTAAAGAAGCATTTAGATACTTTCCTTAAAG   175
  A  F  H  Q  E  Q  G  H  Q  L  L  K  K  H  L  D  T  F  L  K

GCAAGAGTGGACTGAGGGTATTTTTTCCTCTTTGCGGAAAAGCGGTTGAGATGAAATGGT   235
  G  K  S  G  L  R  V  F  F  P  L  C  G  K  A  V  E  M  K  W  F

TTGCAGACCGGGGACACAGTGTAGTTGGTGTGGAAATCAGTGAACTTGGGATACAAGAAT   295
    A  D  R  G  H  S  V  V  G  V  E  I  S  E  L  G  I  Q  E  F

TTTTTACAGAGCAGAATCTTTCTTACTCAGAAGAACCAATCACCGAAATTCCTGGAACCA   355
    F  T  E  Q  N  L  S  Y  S  E  E  P  I  T  E  I  P  G  T  K

AAGTATTTAAGAGTTCTTCGGGGAACATTTCATTGTACTGTTGCAGTATTTTTGATCTTC   415
      V  F  K  S  S  S  G  N  I  S  L  Y  C  C  S  I  F  D  L  P

CCAGGACAAATATTGGCAAATTTGACATGATTTGGGATAGAGGAACATTAGTTGCCATTA   475
      R  T  N  I  G  K  F  D  M  I  W  D  R  G  T  L  V  A  I  N

ATCCAGGTGATCGCAAATGCTATGCAGATACAATGTTTTCCCTCCTGGGAAAGAAGTTTC   535
       P  G  D  R  K  C  Y  A  D  T  M  F  S  L  L  G  K  K  F  Q
```

FIG. 14A

```
AGTATCTCCTGTGTGTTCTTTCTTATGATCCAACTAAACATCCAGGTCCACCATTTTATG    595
  Y  L  L  C  V  L  S  Y  D  P  T  K  H  P  G  P  P  F  Y  V

TTCCACATGCTGAAATTGAAAGGTTGTTTGGTAAAATATGCAATATACGTTGTCTTGAGA    655
  P  H  A  E  I  E  R  L  F  G  K  I  C  N  I  R  C  L  E  K

AGGTTGATGCTTTTGAAGAACGACATAAAAGTTGGGGAATTGACTGTCTTTTTGAAAAGT    715
  V  D  A  F  E  E  R  H  K  S  W  G  I  D  C  L  F  E  K  L

TATGTCTACTTACAGAAAAGTAAATGAGACATAGATAAAATAAAATCACACTGACATGTT    775
  C  L  L  T  E  K  *
```

FIG. 14B

```
  1  GTAGGTTGAA TACTACATCT GCACTTTAAA AAATTTGAAT GCTTGCCAGG
 51  CAGTGCAGGC ATGGGAGTGG AGGTGTCTTC CTCACTCTCT TCCTCCTGTG
101  TAACATCCAC AAAGCATTTT TTTGAATGTC TGTTCTGCAG ATATTTTTAT
151  TACACACTCG TCTGCACACT TTAATGTGTT TTGTCTTTGG TTAGCTCCCA
201  AACTATGGGA AACTGAGGCA GCTAGGGAAA AAGAAAGGTG AGTAAGACAG
251  TGTCTTCTAC CTTGCACCTG GCCTGTAAT AGAAATGAAT TTCAAGTAGC
301  CAAGGGAGAT AAGAGCTCAT CTCCTGAAAG TCCCTGATAC CTGAGCCAGA
351  GGCTGGGGGC AGAGTTGTTG CACACTGTCC TTTGTTCCTT CTTCATGTCC
401  CCAAATCATA ACAGAGTGGG GAGGCTGCTG CCACAGGCTC CTAAAACCAT
451  GAGGGGATGG ACAGCTCTCC ACACCCAGGT CCACACATTC CTCTAGGAGG
501  AAACGCAGAC GTGAGATCCT AATACCTTGA CGATTGTTGA AGTACCAGCA
551  TGCACCATGG GGGACGCTGC TCATCTTCTT AAAGATTTGA TTTTTCTCCC
601  ATAAAATGTT TTTTCTCTTT CTGGTAG
```

FIG.15

```
ATA ACA GAG TGG GGA GGC TGC
```

FIG.16

IDENTIFICATION OF TWO NOVEL MUTANT ALLELES OF HUMAN THIOPURINE S-METHYLTRANSFERASE, AND DIAGNOSTIC USES THEREOF

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under National Cancer Institute grants (R37 CA36401, Leukemia Program Project Grant CA20180, and Cancer Center Grant CA21765). The U.S. Government has certain rights in this invention.

BACKGROUND OF THE INVENTION

1. Field of the Invention

The present invention is in the field of cancer therapeutics, diagnostics, and drug metabolism. In particular, the present invention relates to characterization of the genetic basis for thiopurine methyltransferase deficiency. Three separate point mutations are, at least in part, responsible for severe hematopoietic toxicity in cancer patients who are treated with standard dosages of 6-mercaptopurine, 6-thioguanine or azathioprine.

2. Related Art

Thiopurine methyltransferase (TPMT, E.C. 2.1.1.67) is a cytoplasmic enzyme that preferentially catalyzes the S-methylation of aromatic and heterocyclic sulfhydryl compounds, including the anticancer agents 6-mercaptopurine (6MP) and 6-thioguanine, and the immunosuppressant azathioprine. TPMT activity exhibits genetic polymorphism, with approximately 89% of Caucasians and African-Americans having high TPMT activity, 11% intermediate activity (presumed heterozygotes), and approximately one in 300 inheriting TPMT-deficiency as an autosomal recessive trait. (Weinshilboum, R. M. and Sladek, S. L., *Am. J. Hum. Genet.* 32:651–662 (1980); McLeod, H. L. et al., *Clin. Pharmacol. Ther.* 55:15–20 (1994)). TPMT activity is typically measured in erythrocytes, as the level of TPMT activity in human liver, kidney, lymphocytes and leukemic lymphoblast correlates with that in erythrocytes (Van Loon, J. A. and Weinshilboum, R. M., *Biochem. Genet.* 20:637–658 (1982); Szumlanski, C. L., et al., *Pharmacogenetics* 2:148–159 (1992); McLeod, H. L. et al., *Blood* 85:1897–1902 (1995)).

Mercaptopurine, thioguanine, and azathioprine are prodrugs with no intrinsic activity, requiring intracellular conversion to thioguanine nucleotides (TGN), with subsequent incorporation into DNA, as one mechanism of their antiproliferative effect (Lennard, L., *Eur. J. Clin. Pharmacol* 43:329–339 (1992)). Alternatively, these drugs are metabolized to 6-methyl-mercaptopurine (MeMP) or 6-methylthioguanine (MeTG) by TPMT or to 6-thiouric acid (6TU) by xanthine oxidase; MeMP, MeTG, and 6TU are inactive metabolites. Thus, metabolism of 6MP, azathioprine, or thioguanine by TPMT shunts drug away from the TGN activation pathway. Clinical studies with 6MP and azathioprine have established an inverse correlation between erythrocyte TPMT activity and erythrocyte TGN accumulation, indicating that patients who less efficiently methylate these thiopurines have more extensive conversion to thioguanine nucleotides (Lennard, L., et al., *Lancet* 336:225–229 (1990); Lennard, L. et al., *Clin. Pharmacol. Ther.* 46:149–154 (1989)). Moreover, patients with TPMT deficiency accumulate significantly higher erythrocyte TGN if treated with standard dosages of 6MP or azathioprine, leading to severe hematopoietic toxicity, unless the thiopurine dosage is lowered substantially (e.g. 8–15 fold reduction) (Evans, W. E., et al., *J. Pediatr.* 19:985–989 (1991); McLeod, H. L., et al., *Lancet* 341:1151 (1993); Lennard, L., et al., *Arch. Dis. Child.* 69:577–579 (1993)). The majority of such patients are identified only after experiencing severe toxicity, even though prospective measurement of erythrocyte TPMT activity has been advocated by some (Lennard, L. et al., *Clin. Pharmacol. Ther.* 41:18–25 (1987)). Unfortunately, TPMT assays are not widely available and newly diagnosed patients with leukemia or organ transplant recipients are frequently given erythrocyte transfusions, precluding measurement of their constitutive TPMT activity before thiopurine therapy is initiated. Alternatively, if the inactivating mutations of the human TPMT gene can be identified, PCR-based methods can be developed to determine TPMT genotype and prospectively predict phenotype, as is now possible for drug metabolizing enzymes such as debrisoquin-hydroxylase (Heim, M. and Meyer, U. A., *Lancet* 336:529–532 (1990)) and N-acetyltransferase (Grant, D. M., *Pharmacogenetics* 3:45–50 (1993)).

Identification of the predominant mutations at the TPMT locus would not only offer a strategy for prospectively identifying heterozygotes and TPMT-deficient patients based on their genotype, prior to treatment with potentially toxic dosages of mercaptopurine, azathioprine and thioguanine, it would also provide important insights into the molecular mechanisms of this genetic polymorphism.

SUMMARY OF THE INVENTION

The invention relates to the discovery of three point mutations in exons of TPMT which cause substitutions in the amino acid sequence of TPMT. The presence of these mutant alleles is directly correlated with potentially fatal hematopoietic toxicity when patients are treated with standard dosages of mercaptopurine, azathioprine, or thioguanine.

Based on the discovery of these mutations, a method has been developed for detecting these inactivating mutations in genomic DNA isolated from individual patients (subjects), to make a diagnosis of TPMT-deficiency, or to identify heterozygous individuals (i.e., people with one mutant gene and one normal gene), having reduced TPMT activity. The present invention, therefore, provides a diagnostic test to identify patients with reduced TPMT activity based on their genotype. Such diagnostic test to determine TPMT genotype of patients is quiet advantageous because measuring a patient's TPMT activity has many limitations. Based on this information, three different tests, one to detect the G238C mutation in the TPMTA allele, another to detect G460A mutation in the TPMTB allele, and the third to detect the A719G mutation in the TPMTB allele, have been developed. These tests involve PCR-based amplification of the region of the TPMT gene where the mutations of interest are found. Following amplification, the amplified fragment is assayed for the presence or absence of the specific mutation of interest (i.e., at least one of the three listed above). Although much of these assays can be done "by hand", e.g. sequencing oligonucleotide PCR primers, using a thermocycler and protocol to assay for the presence or absence of a mutation, automated procedures and kits are designed that contain all the reagents, primers, solutions, et cetera for the genotyping test to facilitate the procedure for use in general clinical laboratories such as those found in a typical hospital, clinic or even commercial reference labs.

A preferred embodiment of the present invention relates to the discovery of an intron sequence of the TPMT gene.

Using the sequence of this intron, a primer was made and used to detect A460G mutation of the TPMTB allele in genomic DNA (see Example 2, Detection of A460G mutation of the TPMTB allele in genomic DNA). Amplifying a fragment with intron sequences confirmed that the TPMTB mutations are in fact present in the actual TPMT gene and are not mutations in a pseudogene.

In particular, the invention relates to isolated polynucleotide molecules comprising a mutant allele of thiopurine S-methyltransferase (TPMT) or a fragment thereof, which is at least ten consecutive bases long and contains a point mutation in at least one of the cDNA positions 238, 460, or 719. The point mutation at cDNA position 238 is a cytosine substitution for guanine and the whole polynucleotide has the sequence shown in FIG. 11. The point mutation at cDNA position 460 is an adenine substitution for guanine and the whole polynucleotide has the sequence shown in FIG. 12. The point mutation at cDNA position 719 is a guanine substitution for adenine and the whole polynucleotide has the sequence shown in FIG. 13.

The invention also relates to an isolated polynucleotide molecule comprising a mutant allele of thiopurine S-methyltransferase (TPMT) or a fragment thereof, which is at least 260 consecutive bases long and contains a point mutation at cDNA position 460 and a point mutation at cDNA position 719. The point mutation at position 460 is an adenine substitution for guanine and the point mutation at position 719 is a guanine substitution for adenine, and the sequence of the whole polynucleotide molecule is shown in FIG. 14.

An aspect of the invention relates to polynucleotide molecules complementary to any one of the polynucleotide molecules described above.

Another aspect of the invention relates to purified peptides encoded by the polynucleotide molecules, described above, as well as antibodies raised against these peptides.

A different aspect of the invention relates to a diagnostic assay for determining thiopurine S-methyl-transferase (TPMT) genotype of a person which comprises isolating nucleic acid from said person; amplifying for a thiopurine S-methyltransferase (TPMT) PCR fragment from said nucleic acid, which includes at least one of cDNA positions 238, 460, or 719, thereby obtaining an amplified fragment; and sequencing the amplified fragment thereby determining the thiopurine S-methyltransferase (TPMT) genotype of said person.

Another embodiment of the invention relates to a diagnostic assay for determining thiopurine S-methyl-transferase (TPMT) genotype of a person which comprises isolating nucleic acid from said person; amplifying for a thiopurine S-methyltransferase (TPMT) PCR fragment from said nucleic acid, which includes at least one of cDNA positions 238, 460, or 719, thereby obtaining an amplified fragment; and treating the amplified DNA fragment with CviRI in its corresponding restriction buffer to detect presence or absence of a point mutation at cDNA position 238, MwoI in its corresponding restriction buffer to detect presence or absence of a point mutation at cDNA position 460, or AccI in its corresponding restriction buffer to detect presence or absence of a point mutation at cDNA position 719, thereby determining the thiopurine S-methyltransferase (TPMT) genotype of said person. In a preferred embodiment of the invention, controls are run parallel to the above described reaction steps, wherein cDNA, which is wild-type for TPMT sequence, is amplified for a wild-type TPMT fragment, thereby obtaining a wild-type TPMT fragment; and treating the wild-type TPMT fragment with CviRI in its corresponding restriction buffer, MwoI in its corresponding restriction buffer, or AccI in its corresponding restriction buffer.

A further aspect of the invention relates to a diagnostic assay for determining thiopurine S-methyl-transferase (TPMT) genotype of a person which comprises isolating nucleic acid from said person; making a first and a second PCR primer wherein the first PCR primer is complementary to a region 5' to one of three point mutation sites at cDNA positions 238, 460, or 719; and the second PCR primer is complementary to a region 3' to the same one of the three point mutation sites at cDNA positions 238, 460, or 719; amplifying the sequence in between the first and the second primers; thereby obtaining an amplified fragment; and treating the amplified fragment with CviRI in its corresponding restriction buffer to detect presence or absence of a point mutation at cDNA position 238, MwoI in its corresponding restriction buffer to detect presence or absence of a point mutation at cDNA position 460, or AccI in its corresponding restriction buffer to detect presence or absence of a point mutation at cDNA position 719, thereby determining the thiopurine S-methyltransferase (TPMT) genotype of said person.

A preferred embodiment of the invention relates to a diagnostic assay for determining thiopurine S-methyltransferase (TPMT) genotype of a person which comprises isolating nucleic acid from said person; amplifying for a thiopurine S-methyltransferase (TPMT) PCR fragment from said nucleic acid using a first and a second set of primers in a first and a second PCR reaction, respectively; wherein the first set of primers contains primer X and primer Y, and the second set of primers contains primer X and primer Z; wherein the Y primer is complementary to a region 5' to one of three point mutation sites at cDNA positions 238, 460, or 719, and includes the wild type nucleotide for said cDNA position; the Z primer is identical to the Y primer except that instead of the wild type nucleotide, it contains the respective mutant nucleotide at the respective cDNA positions 238, 460, or 719; and the X primer is complementary to a region 3' to the point mutation site corresponding to primers Y and Z; amplifying the sequence in between primers X and Y and in between primers X and Z; thereby obtaining an amplified fragment in each of the first and the second PCR reactions; and visualizing the contents of the first and the second PCR reactions, thereby determining the thiopurine S-methyltransferase (TPMT) genotype of said person. The size of the amplified fragment needs only be large enough so that it is detectable. A preferred range of the amplified fragment size is from 15 nucleotides to several hundreds, more preferably from 75 to 400, and most preferably from 80 to 260.

Another aspect of the invention relates to a diagnostic kit for determining thiopurine S-methyltransferase (TPMT) genotype of a person comprising a carrier means having in close confinement therein at least two container means, wherein a first container means contains a first polynucleotide molecule described above, which contains at least one of the point mutations at cDNA positions 238, 460, or 719 and which contains the whole or part of the sequence shown in FIGS. 11–14, and a second container means contains a second polynucleotide molecule encoding a wild-type allele of thiopurine S-methyltransferase (TPMT) or a fragment thereof which is at least ten consecutive bases long and contains at least one of cDNA positions 238, 460, or 719, corresponding to the first polynucleotide of the first container means.

A further aspect of the invention relates to an isolated polynucleotide molecule having a sequence shown in FIG.

15, SEQ ID NO:9, or a fragment thereof which is at least ten bases long. In a preferred embodiment of the invention, the polynucleotide molecule has the nucleotide sequence identified as SEQ ID NO:10. Moreover, the invention relates to an isolated polynucleotide molecule complementary to the polynucleotide molecule having a sequence shown in FIG. 15.

BRIEF DESCRIPTION OF THE FIGURES

(FIG. 2A) Autoradiographs of hybridizations with the wild-type TPMT cDNA (Lower), followed by the h28S ribosomal oligonucleotide probe (Upper), of total RNA from human liver (lane 1), leukocytes of unrelated individuals (controls, lanes 2 and 3), the TPMT-deficient patient (lane 5), and her father (lane 4) and mother (lane 6). (FIG. 2B) Relative level of the two major TPMT mRNA transcripts after normalization to the 28S rRNA signal. (FIG. 2C) Erythrocyte TPMT activities determined for the propositus [deficient patient (Pt.)], her parents, and unrelated controls. NA, not available.

(FIG. 3A) Nucleotide sequence analysis of the fragment of the wild-type and the mutant clones derived from reverse transcription-PCR products of total RNA isolated from leukocytes. The adenine residue in the initiation codon is number +1. (FIG. 3B) Wild-type and mutant TPMT cDNA sequence (nt 232–243) and deduced amino acid sequence of the protein encoded. The mutation site is underlined.

(FIG. 4A) Hybridization with 18S rRNA-specific y18S oligonucleotide labeled with [γ-$^{32}$P]ATP. (FIG. 4B) Hybridization with TPMT cDNA probe labeled with [α-$^{32}$P]ATP. (FIG. 4C) Mean TPMT activity in yeast lysates (duplicate experiments). wt, Wild type; mut, mutant; cont., control.

FIG. 6A depicts a Western blot of RBC lysates probed by anti-TPMT antibodies. Lysate equivalent to 2×10$^6$ RBC was loaded in lanes 2 and 3. Yeast lysate expressing wild-type TPMT was utilized for comparison (lane 1). FIG. 6B depicts relative levels of TPMT protein and activities in erythrocytes determined by densitometry on the Western blot and radiochemical methods, respectively.

FIG. 7A depicts nucleotide 454–465 and FIG. 7B depicts nucleotide 712–723. The adenine residue in the initiation codon is number +1.

FIG. 8A depicts wild-type cDNA as control; FIG. 8B depicts TPMT-deficient patient; FIG. 8C depicts father; and FIG. 8D depicts mother.

FIG. 9A depicts Northern blot of yeast total RNA hybridized with TPMT cDNA probe and subsequently stripped and reprobed with y 8S rRNA-specific oligonucleotide; FIG. 9B depicts Western blot of yeast lysates (0.25 μg for lanes 1–5, 25 μg for lane 6) with anti-TPMT antibodies; FIG. 9C depicts TPMT activities measured by in vitro incubation of yeast lysates with substrate concentrations of 10 μM 6MP and 1 mM SAM.

FIG. 10A depicts TPMT activities expressed as a percentage of those obtained at 37° C., 0 hr (i.e. 83.7, 142.5, 88.6 nmol/min/mg TPMT for wild-type, TPMT$_{460}$, and TPMT$_{719}$ lysates, respectively). FIGS. 10B–10D depict immunoreactive protein with equal loading of wild-type. FIG. 10B depicts wild type protein; FIG. 10C depicts TPMT$_{460}$; and FIG. 10D depicts TPMT$_{719}$; respectively.

FIG. 11 depicts the cDNA and deduced amino acid sequences of G238C mutant TPMT (TPMTA) (SEQ ID NO:1–2).

FIG. 12 depicts the cDNA and deduced amino acid sequences of G460A mutant TPMT (SEQ ID NO:3–4).

FIG. 13 depicts the cDNA sequences of A719G mutant TPMT (SEQ ID NO:5–6).

FIG. 14 depicts the cDNA and deduced amino acid sequences of TPMTB mutant (SEQ ID NO:7–8).

FIG. 15 depicts a partial sequence of a TPMTB intron (SEQ ID NO:9).

FIG. 16 depicts a primer comprised of an intron sequence (SEQ ID NO:10).

DETAILED DESCRIPTION OF THE PREFERRED EMBODIMENTS

Figure 1:
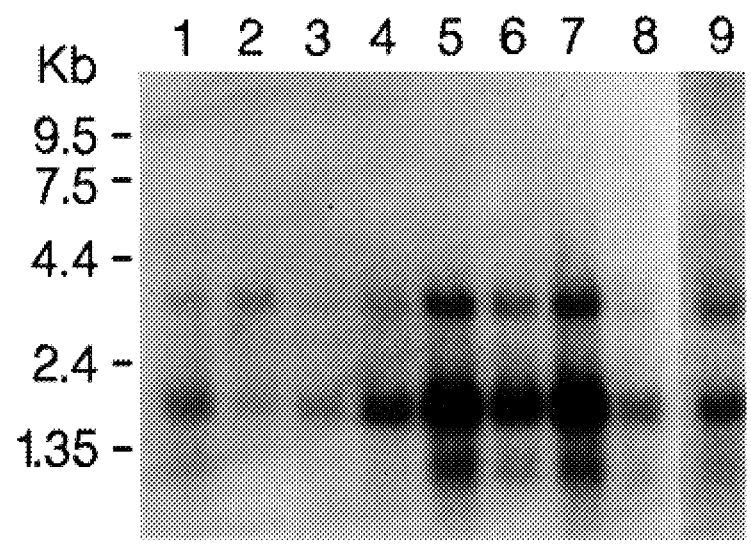
FIG. 1 depicts Northern blot analysis of poly(A)$^+$ RNA isolated from various human tissues and hybridized with wild-type (SEQ ID NO:11–12) TPMT cDNA, demonstrating the presence of multiple TPMT mRNAs. Each lane contained ≈2 μg of poly(A)$^+$ RNA. Lanes:1, heart; 2, brain; 3, placenta; 4, lung; 5, liver; 6, skeletal muscle; 7, kidney; 8, pancreas; 9, peripheral blood leukocytes.

The autosomal recessive trait of thiopurine S-methyltransferase (TPMT) deficiency is associated with potentially fatal hematopoietic toxicity when patients are treated with standard dosages of mercaptopurine, azathioprine or thioguanine. Three different point mutations in exons of TPMT are described herein. The first mutation (TPMTA) is a point mutation identified at cDNA position 238 ($G^{238} \rightarrow C$), which results in an amino acid change at codon 80 ($Ala^{80} \rightarrow Pro$). This amino acid substitution decreases the enzymatic activity of TPMTA approximately 100-fold. The allele containing this G238C mutation is designated as TPMTA. The predominant mutant allele associated with human TPMT-deficiency was identified and defined as (TPMTB). This mutant allele involves two nucleotide transitions with amino acid changes at cDNA position 460 ($G^{460} \rightarrow A$), codon 154 ($Ala^{154} \rightarrow Thr$), and cDNA position 719 ($A^{719} \rightarrow G$), codon 240 ($Tyr^{240} \rightarrow Cys$). Heterologous expression established that either mutation in TPMTB alone leads to a reduction in catalytic activity, while both mutations lead to complete loss of activity. The mutations at cDNA positions 238 and 460 eliminate the recognition site for CviRI and MwoI, respectively, while A719G adds an AccI restriction site. TPMTB was detected in genomic DNA of 18 out of 25 (72%) of Caucasians with heterozygous phenotypes, indicating that TPMTB is the most prevalent mutant allele associated with TPMT-deficiency.

Based on the sequence of the mutant alleles provided herein, PCR primers are constructed that are complementary to the region of the mutant allele encompassing the point mutation. A primer consists of a consecutive sequence of polynucleotides complementary to any region in the allele encompassing the position which is mutated in the mutant allele. PCR primers complementary to a region in the wild-type allele corresponding to the mutant PCR primers are also made to serve as controls in the diagnostic methods of the present invention. The size of these PCR primers range anywhere from five bases to hundreds of bases. However, the preferred size of a primer is in the range from 10 to 40 bases, most preferably from 15 to 32 bases. As the size of the primer decreases so does the specificity of the primer for the targeted region. Hence, even though a primer which is less than five bases long will bind to the targeted region, it also has an increased chance of binding to other regions of the template polynucleotide which are not in the targeted region and do not contain the mutated base. Conversely, a larger primer provides for greater specificity, however, it becomes quite cumbersome to make and manipulate a very large fragment. Nevertheless, when necessary, large fragments are employed in the method of the present invention.

To amplify the region of the genomic DNA of the individual patient who may be a carrier for the mutant allele, primers to one or both sides of the targeted position, i.e. the cDNA positions 238, 460, or 719, are made and used in a PCR amplification reaction, using known methods in the art (e.g. 2 Massachusetts General Hospital & Harvard Medical School, *Current Protocols In Molecular Biology*, Chapter 15 (Green Publishing Associates and Wiley-Interscience 1991); for the preferred protocols and methods see the Materials and Methods section for Examples 1 and 2).

According to the method of the present invention, once an amplified fragment is obtained, it can be analyzed in several ways to determine whether the patient has a mutant allele of the TPMT gene. For example, the amplified fragment can be simply sequenced and its sequence compared with the wild-type cDNA sequence of TPMT. If the amplified fragment contains one or more of the point mutations described in the present invention, the patient is likely to have TPMT-deficiency or be a heterozygote (i.e., reduced activity) and therefore, develop hematopoietic toxicity when treated with standard amounts of mercaptopurine, azathioprine, or thioguanine. Alternatively, a combination of PCR fragment amplification and RFLP analysis is used to determine TPMT genotype of the individual.

In a preferred embodiment of the invention, a fragment of the genomic DNA of the patient is amplified by making a primer containing the mutation site, i.e. cDNA positions 238, 460, or 719. Each amplified fragment, as well as the fragments generated against the wild-type cDNA, are treated with the corresponding restriction endonuclease (i.e., CviRI for fragment amplified for cDNA position 238; MwoI for fragment amplified for cDNA position 460; AccI for fragment amplified for cDNA position 719) in the presence of the appropriate cutting buffer for each enzyme. The preferred buffers are those recommended by the manufacturer of the restriction enzyme. After the fragments have been incubated in the restriction reaction mixtures at the recommended temperatures, and restriction reactions have been allowed to proceed to completion, they are electrophoresed on a gel, e.g. a 2% agarose gel. The size of the fragments are measured using standard ladder size-markers. If the amplified fragments are not cut with either CviRI or MwoI, it indicates that the genomic DNA of the patient contains a mutation at cDNA positions 238 and/or 460, respectively. If the fragment is cut with the restriction enzyme AccI, however, it indicates that the genomic DNA which was amplified at the region encompassing cDNA position 719 contains the 719 mutation.

When a single primer encompassing a mutation site is used, it is preferred to (1) simply sequence the amplified fragment, (2) use conditions where PCR-amplification will occur only when one of the mutations is present in genomic DNA or the cDNA fragment (i. e., mutation specific PCR (MSPCR)), or (3) use RFLP analysis to determine the TPMT genotype of a subject.

In the MSPCR method, DNA of the patient, as well as a control, is amplified separately, using a wild type and a mutation-containing primer. The content of each amplification vial (containing wild type or mutant type primer) is then examined for the presence of amplified DNA. For example, equal aliquot of a DNA intercalating dye, such as ethidium bromide, is added to each vial and any DNA present therein is visualized. A method of visualization includes electrophoresing the contents of each amplification vial (i.e., control DNA+wild type primer, control DNA+primer containing specific mutation, patient's genomic DNA+wild type primer, patient's genomic DNA+primer containing specific mutation), staining the electrophoresis gel with ethidium bromide, shining UV light on the gel, and looking for the presence or absence of an amplified band in each lane. As an example, presence of a band in the lane containing patient's genomic DNA+wild type primer, as well as a band in the lane containing patient's genomic DNA+primer containing specific mutation indicates that the patient is heterozygote for the TPMT allele. The control experiment allows confirmation of the accuracy of the test. For example, control DNA from an individual who is known to be homozygote for TPMT wild type is amplified as described above and the results are analyzed as follows. Presence of a band in the lane containing control DNA+wild type and absence of a band in the lane containing control DNA+primer indicates that the particular mutation, which is encompassed in the sequence of the mutant type primer, does not exist on either of the TPMT alleles of the control DNA as expected.

If it is desired to use RFLP to analyze the amplified polynucleotides, a sequence of non-TPMT derived polynucleotides (not complementary to the TPMT gene) is added to the end of the primer. For example, the non-TPMT derived sequence of polynucleotides is added to the 5' end of the primer. Hence, the size of the amplified fragment is sufficiently increased so that if the fragment is cut with a restriction enzyme, the sub-fragments generated are sufficiently large to be detected.

In another preferred embodiment of the invention, two common primers are used, each of which is complementary to either side of the mutation site. Common primers are those which do not encompass the mutation sites, i.e. their sequences are common to both the wild-type and the mutant alleles. The primers are elongated in opposite directions so that they amplify a relatively large fragment encompassing the site of mutation. This fragment is subsequently analyzed by RFLP analysis. As described above, presence of G238C or G460A will destroy the CviRI and MwoI recognition sites, hence, a fragment containing these mutations does not cut with the corresponding restriction enzyme. On the other hand, presence of A719G results in the creation of a recognition site for AccI, hence, a fragment containing this mutation is cut with this enzyme.

Alternatively, PCR conditions and primers are developed which amplify only when the target mutation is present (FIG. 5), or when only the wild-type sequence is present at the mutation site (i.e., allele specific PCR (ASPCR) amplification or mutation specific PCR (MSPCR) amplification).

To determine whether the individual is homozygous or heterozygous for TPMT, the mutation sites on the genomic DNA are amplified separately by using wild-type and mutant primers. If only a wild-type or a mutant-type fragment is amplified, the individual is homozygous for the wild-type or the particular mutant-type TPMT. However, presence of more than one type of fragment indicates that the individual is heterozygous for TPMT allele.

An example of a diagnostic assay that is carried out according to the present invention to determine the TPMT genotype of a person is as follows. This example is provided for illustrative purposes and is not meant to be limiting.

Tissue containing DNA (e.g., not red blood cells) from the subject is obtained. Examples of such tissue include white blood cells, mucosal scrapings of the lining of the mouth, epithelial cells, pancreatic tissue, liver, et cetera. Genomic DNA of the individual subject is isolated from this tissue by the known methods in the art, such as phenol/chloroform extraction. Six vials, numbered 1–6, are set up with each containing an equal aliquot of the genomic DNA of the subject. PCR primers encompassing cDNA positions 238 (both wild-type and G238C mutant), 460 (both wild-type and G460C mutant), and 719 (both wild-type and A719G mutant) are synthesized. The primers are preferably 10–40 bases long, most preferably 15–31 bases long. Each type of primer pair (wild-type and mutant) is added to only one of the vials 1–6, and using a standard PCR procedure, a TPMT fragment in each of the six vials is amplified. Next, the content of each vial is analyzed by the various methods described above, which include RFLP analysis, sequencing, mutation-specific amplification, or a combination of such methods.

In a different embodiment of the invention, the mutant alleles of the present invention are used to express mutant proteins. For example, the mutant proteins are produced in an expression system such as yeast, bacterial, or mammalian cell systems. To do so, recombinant plasmids are constructed that contain yeast GAL10-CYC1 promoter and mutant form of TPMT cDNA, and a PGK terminator. After introduction of the vector into the yeast cells, GAL10-CYC1 promoter is induced by galactose. TPMT protein is obtained from the yeast cell lysates. If desired, the proteins may be purified by known methods in the art, such as DEAE ion exchange chromatography (Van Loon, J. A., and R. M. Weinshilboum, *Drug Metab. Dispos.* 18:632–638 (1990)), gel filtration chromatography using for example, Sephadex G-100 Superfine as described by Van Loon, J. A., and R. M. Weinshilboum, *Drug Metab. Dispos.* 18:632–638 (1990), as well as hydroxylapatite chromatography (Van Loon, J. A. et al., *Biochem. Pharmacol.* 44:775–785 (1992)).

The mutant proteins are used in a variety of diagnostic assays and methods. For example, they are used to test whether a given therapeutic drug can be metabolized by the mutant proteins. This assay allows development of medicaments which, like 6-mercaptopurine, 6-thioguanine, or azathioprine, are effective against a given cancer or useful in preventing rejection of a transplant, yet do not cause the severe toxicity which is brought about by said drugs in patients who have TPMT-deficiency. In this assay, the drug which is being tested is incubated under simulated physiological conditions (for example in isolated body fluid such as plasma or blood and at body temperature) for various lengths of time. At various time-points aliquots are removed and analyzed for presence or absence of the drug or its expected byproduct(s) to determine whether and when the drug is properly metabolized.

In another embodiment of the invention, the mutant proteins are used to raise antibodies according to known methods routinely used by the artisans. The term "antibody" refers both to monoclonal antibodies which have a substantially homogeneous population and to polyclonal antibodies which have heterogeneous populations. Polyclonal antibodies are derived from the antisera of animals immunized with the analyte. Monoclonal antibodies to specific TPMT mutants may be obtained by methods known in the art. See, for example Kohler and Milstein, *Nature* 256:495–497 (1975). Such antibodies may be of any immunoglobulin class including IgG, IgM, IgE, IgA, IgD and any subclass thereof. The term "antibody" is meant to include both intact molecules as well as fragments thereof, such as Fab and F(ab')$_2$, which are capable of binding antigen.

The term "analyte" in this context refers to not only the intact mutant TPMT protein but also to any fragment of the protein which contains an antigenic site capable of binding to an antibody and which antigenic site is present in the mutant protein but lacking from the wild-type protein. Such analytes are prepared by a routine method in which a series of shortened peptides are expressed recombinantly, for example in the same way that the whole mutant proteins are expressed in yeast. The shortened peptides are made by for example, progressively deleting one codon, either on the 5' or the 3' end of the coding region of the mutant cDNA, yet preserving the mutated codon, before it is inserted into the expression vector. Hence, a number of peptides are produced that are progressively smaller in size by one amino acid, yet contain the mutation. Antibodies are raised against these peptides as well as the whole mutant protein. The antibodies are tested for their ability to distinguish wild-type TPMT from the mutant TPMT proteins by a standard immunoassay method such as ELISA (2 Massachusetts General Hospital & Harvard Medical School, *Current Protocols In Molecular Biology*, Chapter 11 (Green Publishing Associates and Wiley-Interscience 1991)), using recombinantly expressed wild-type TPMT and mutant TPMT proteins.

In a preferred method for making antibodies, mutant cDNA as well as shortened mutant cDNA is expressed using expression vector pGEX-2T (Pharmacia Biotech, Uppsala, Sweden) containing the DNA fragment encoding glutathione S-transferase from *Schistosoma japonicum* to construct a recombinant plasmid with an insert for the uninterrupted coding frame of GST-mutant TPMT fusion protein. Anti-mutant TPMT antibodies are raised in rabbits by immunization with GST-mutant TPMT fusion protein (Rockland Corp., Gilbertsville, Pa.) and then purified by affinity chromatography. The antibodies are purified in sequence (by affinity chromatography) on sepharose with immobilized GST and GST-mutant TPMT. Antibodies so obtained are used in a variety of assays and methods.

The antibodies of the present invention are used in a variety of protein assay methods (such as standard radioimmunoassay using labelled antibodies against protein bound to a membrane, ELISA, et cetera), to determine whether a given individual has a given mutant phenotype. For example, tissue lysate from the patient is obtained from blood, liver, pancreas, or any other tissue expressing TPMT. The presence or absence of the mutant protein is detected using the detectably labelled antibodies of the present invention. Of course, the lysate may be crude or purified to various extent. Hence, an efficient and simple method of obtaining information regarding the TPMT genotype in the patient is now made available which aids the physician in choosing the therapeutic modality for the patient.

In a preferred embodiment of the invention, an intron sequence of the TPMT gene is disclosed (see FIG. 16). Using the intron fragment, probes are made to clone the genomic sequence and define the gene, hence, defining all of the introns in the TPMT gene. Starting from the intron present in the functional TPMT gene (as opposed to a TPMT-like pseudogene present in human genome which interfer with PCR-based detection of inactivating mutations), the sequence and the location of the other introns, as well as the whole structure of the chromosomal gene, is obtained. A useful method for such determination is PCR-based method of DNA walking (Siebert, P. D. et al., *Nucleic Acids Research* 23:1087–1088 (1995)). This method allows walking from a known sequence (e.g., an intron) to uncloned DNA fragments. In this way, sequence information on DNA fragments adjacent to that already known is generated. Another more common technique involves using the DNA fragment encompassing the intron sequence for screening the genomic library (see, e.g., 1 Massachusetts General Hospital and Harvard Medical School, *Current Protocols in Molecular Biology*, Chapter 6 (Green Publishing Associates and Wiely-Interscience 1991). Hence, the complete genomic sequence of TPMT is so determined. The chromosomal location of the gene is determined, using known methods in the art (Lee, D. et al., *Drug Metab. Disp.* 23:398–405 (1995)). It should be noted that the presence of multiple TPMT-like pseudogene sequences in the human genome precludes using the known cDNA sequence for direct cloning of TPMT functional gene.

By defining the intron and exon structures, sequences and locations for the human gene encoding thiopurine S-methyltransferase (TPMT), a complete understanding of the genetic basis for TPMT-deficiency in humans is developed. The role of splice-site mutations resulting in RNA splicing defects, as a basis for loss of TPMT activity, is defined using this information. Moreover, using the sequence and location of introns, oligonucleotide primers for intron sequences are synthesized and PCR-based methods are developed that are specific for the human gene which encodes TPMT (versus pseudogenes). Accordingly, more specific diagnostic tests are developed to detect the presence of mutations or wild-type TPMT sequences in genomic DNA. Since the intron and exon structure of human TPMT can now be detected, efficient methods to detect mutations at the human TPMT locus, such as single-strand conformation polymorphism (SSCP) analysis, are developed, thus facilitating the identification of new mutations responsible for loss of TPMT activity. Finally, by defining the 5' and 3' untranslated regions of the TPMT gene, it is now possible to understand the genetic regulation of this gene, and thus analyze and predict changes in TPMT protein levels and activity.

The following examples are intended to further illustrate certain preferred embodiments of the invention and are not intended to be limiting in nature.

EXAMPLE 1

Materials and Methods

Human Subjects

Whole blood was obtained from an 8-year-old girl who had recently completed therapy for acute lymphoblastic leukemia and had previously been determined to have an inherited deficiency in TPMT [activity=0.8 unit/ml of packed red blood cells (u/ml pRBC)]. This child had developed severe hematopoietic toxicity with conventional oral dosages of mercaptopurine (75 mg/m$^2$ per day), as described in detail (Evans et al., *J. Pediatr.* 119:985–989 (1991)). Blood samples were also obtained from two healthy female volunteers having erythrocyte TPMT activities consistent with the homozygous wild-type genotype (11 and 19 u/ml pRBC) and from the mother and father of the propositus, who had TPMT activities indicative of a heterozygous genotype (5.6 and 3.6 u/ml PRBC, respectively). Total leukocyte RNA was extracted by the method of Chomczynski and Sacchi (Chomczynski and Sacchi, *Anal. Biochem.* 162:156 (1987)) and DNA was isolated by chloroform/phenol extractions. TPMT phenotype was assigned on the basis of erythrocyte TPMT activity, according to the criteria of Weinshilboum and Sladek (Weinshilboum and Sladek, *Am. J. Hum. Genet.* 32:651–662 (1980)). The studies were approved by the institutional review board for clinical trials at St. Jude Children's Research Hospital, and informed consent was obtained from the participants or their guardians.

Synthesis of cDNA

First-strand cDNA was synthesized, essentially as described (Schuetz et al., *J. Clin. Invest.* 42:1018–1024 (1993)), from 2 $\mu$g of total cellular RNA. The reaction mixture (100 ul) contained 10 mM Tris-HCl (pH 8.3 at 20° C.), 50 mM KCl, 1.5 mM MgCl$_2$, 0.001% (wt/vol) gelatin, 0.2 mM dNTPs, 20 units of RNasin, 200 ng of the random hexamers, and 200 units of Moloney murine leukemia virus reverse transcriptase (SuperScript; GIBCO/BRL) and was incubated at 42° C. for 60 min.

PCR of TPMT Coding Region

PCR primers were synthesized on the basis of the published colon carcinoma TPMT cDNA sequence (FIG. 11, SEQ ID NO:1; Honchel et al., *Mol. Pharmacol.* 43:878–887 (1993)). The sequences of primers used for the first round of amplification and all subsequent PCR amplifications are given in Table 1. Each cycle of amplification consisted of denaturation at 94° C. for 1 min, annealing at 55° C. for 30 sec, and primer extension at 72° C. for 2 min (35 cycles). After amplification, TPMT PCR products were made blunt and the product was cloned into the Sma I site of plasmid pGEM-7Zf(+) (Promega). The inserts present in positive clones were sequenced by automated fluorescence sequencing.

Northern and Southern Blot Hybridization Probes

The wild-type human liver TPMT cDNA, cloned as described above, was used for probe preparation. Oligonucleotide h28S (5'-GCA-CAT-ACA-CCA-AAT-GTC-TGA-ACC-TGC-GGT-3') (SEQ ID NO:23) was homologous to the GenBank AS# M11167.Gb_Pr sequence of human 28S rRNA (bp 4571–4600). Oligonucleotidey 18S (5'-GGC-TTG-AAA-CCG-ATA-GTC-CCT-CTA-AGA-AG-3') (SEQ ID NO:24) was homologous to the GenBank AS# J01353.Gb_Pl sequence of yeast 18S rRNA (bp 1373–1401).

Northern and Southern Blotting

Northern blot analysis was performed on human and yeast total RNA or multiple tissue Northern blots MTN I and II (Clontech). Membranes were hybridized with the radiolabeled TPMT cDNA, stripped, then reprobed with either the h28S or y18S oligonucleotide, in the case of total RNA analysis, or with the human β-actin cDNA (Clontech), in the case of poly(A)⁺ MTN blots. Samples (10 μg per lane) of human genomic DNA isolated from venous blood cells were digested with EcoRI (promega), resolved by 0.8% agarose gel electrophoresis, and transferred to nylon membranes (Magna NT; Micron Separations, Westboro, Mass.). The DNA blots were washed under conditions of high stringency (final wash at 50° C. with 0.1X standard saline citrate).

Site-Specific Mutagenesis of TPMT cDNA

The PCR conditions were as described above except that 100 ng of the cDNA clone served as a template with primers 3 and 4 (Table 1) and 2.5 units of *Pyrococcus furiosum* DNA polymerase for amplification. The coding region of the wild-type or the mutant TPMT cDNA was ligated into pYeDP yeast expression vector. Authenticity of the PCR products was confirmed by sequencing.

Expression in Yeast Cells

Transformation of the yeast strain 2805 was carried out by treatment with lithium acetate (Becker and Lundblad in *Current Protocols in Molecular Biology*, eds. Ausbel et al. (Green & Wiley Interscience, New York), Vol. 2, pp. 13.7.1–13.7.10 (1993)). Yeast cells transformed with recombinant expression vectors were grown on galactose-containing medium, and the lysate and total RNA were prepared as described (Krynetski et al., *FEBS Lett.* 336:87–89 (1993); Schmitt et al., *Nucleic Acids Res.* 18:3091 (1990)). In all experiments on heterologous expression of TPMT, yeast transformed with the expression vector without the TPMT cDNA insert was used as a control. The concentration of protein in yeast lysates was determined by the method of Bradford (Bradford, *Anal. Biochem.* 72:248–254 (1976)).

TPMT Assay

Erythrocyte lysates were analyzed for TPMT activity by the non-chelated radiochemical assay of Weinshilboum et al. (Weinshilboum et al., *Clin. Chim. Acta* 85:323–333 (1978)). Enzymatic activity of yeast lysates was assayed in a total volume of 1 ml, and formation of the S-methylated thiopurine product was determined by HPLC.

Detection of $G^{238} \rightarrow C$ Mutation in Genomic DNA

Mutation-specific primers and reaction conditions were developed to detect the presence or absence of the $G^{238} \rightarrow C$ TPMT mutation in the propositus and her family. Five hundred nanograms of genomic DNA was amplified by PCR using primers 5 and 6 (Table 1). PCR conditions were as follows: denaturation at 94° C. for 1 min, annealing at 64° C. for 45 sec, and elongation at 72° C. for 1 min for 35 cycles. Amplification products were then diluted 1:10 with water and aliquots were separately reamplified by using (i) primers 5 and 7 for wild-type sequence, or (ii) primers 5 and 8 for the mutant sequence (Table 1). Reaction conditions were denaturation at 94° C. for 1 min, annealing at 45° C. for 45 sec, and elongation at 72° C. for 1.5 min. PCR products (5 μl) were analyzed by non-denaturing 8% PAGE.

RFLP Analysis to Detect Mutation in cDNA

TPMT cDNA synthesized by reverse transcription-PCR was used as a template in PCR amplification with primers 5 and 6, for 30 cycles of denaturation at 94° C. for 1 min, annealing at 62° C. for 45 sec, and elongation at 72° C. for 1.5 min. The synthesized DNA fragments were treated with CviRI restriction endonuclease (Megabase Research Products, Lincoln, Nebr.) and analyzed by non-denaturing 8% PAGE.

Data Analysis

The University of Wisconsin Genetics Computer Group software package was used to analyze sequence information and to estimate potential changes in the structure of the mutant protein (Genetics Computer Group (1991) Program Manual for the GCG Package, Version 7, April 1991 (Genetics Computer Group, 575 Science Drive, Madison, Wis. 53711)).

Results

Transcription of TPMT mRNA

Figure 2A:
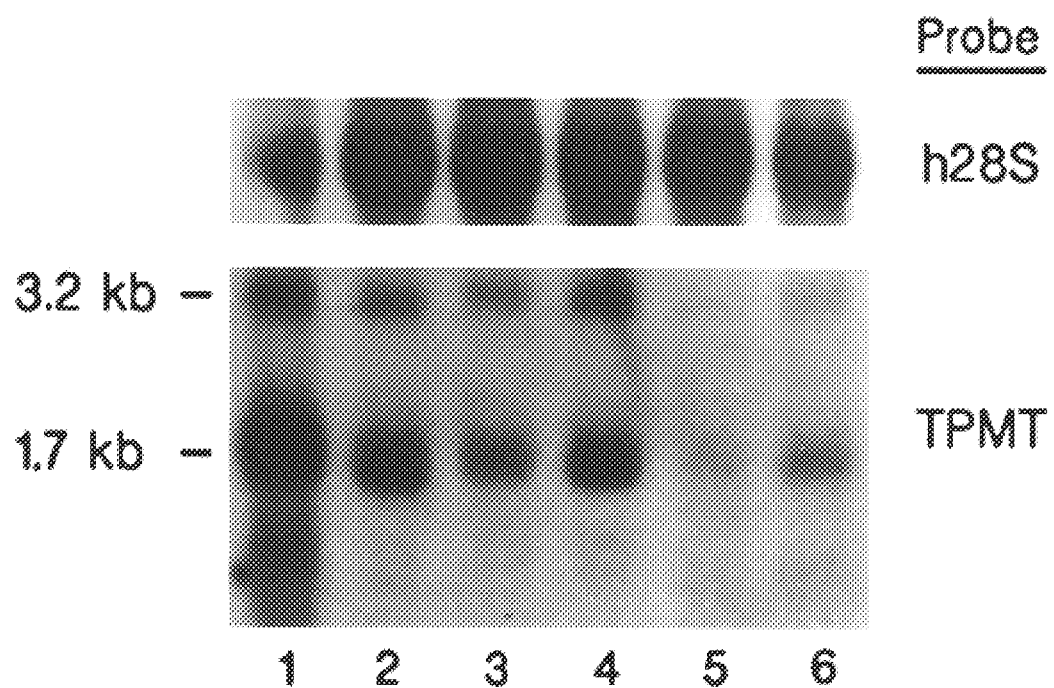
FIGS. 2A, 2B, and 2C depict relative expression of TPMT mRNA and TPMT activity among individuals of differing phenotype.
Figure 2B:
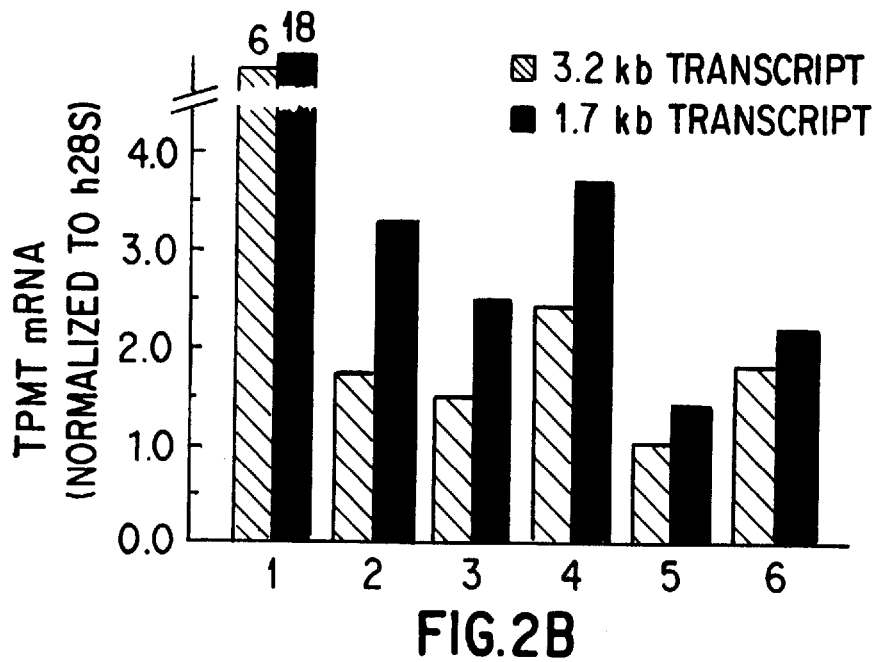
Figure 2C:
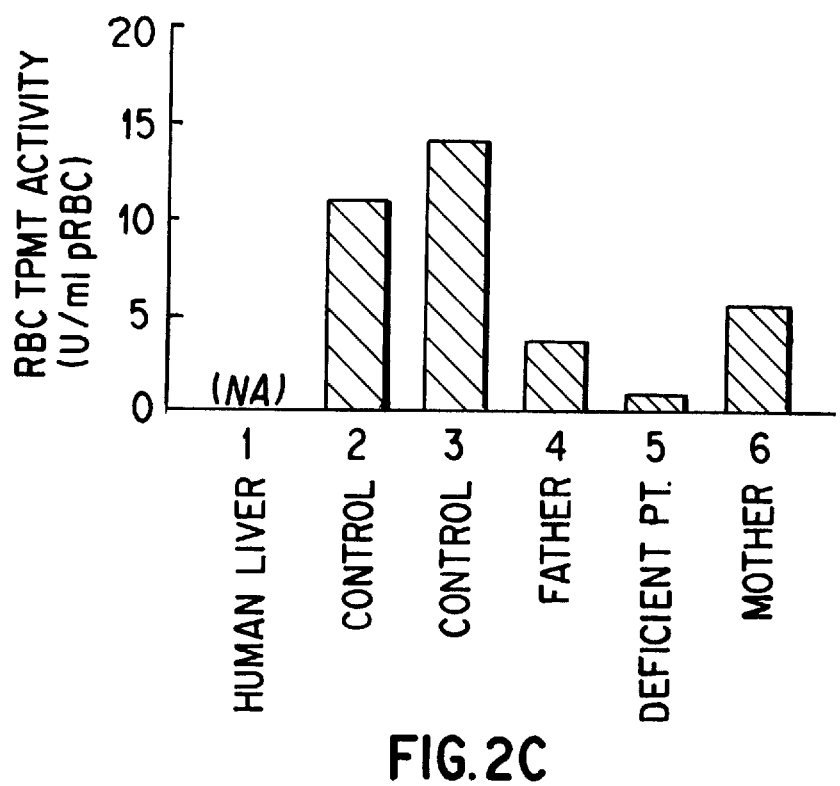

Based on the published (Honchel et al., *Mol. Pharmacol.* 43:878–887 (1993)) wild-type sequence of human colon carcinoma TPMT cDNA, several primers for PCR amplification of the coding region of TPMT cDNA were designed. Human liver TPMT cDNA corresponding to the published TPMT open reading frame (bp −44 to 806; Honchel et al., *Mol. Pharmacol.* 43:878–887 (1993)) was synthesized with primers 1 and 2 (Table 1) and used as a probe for Northern blot analysis of TPMT mRNA in various human tissues, as well as in the leukocytes of the patient and volunteers. Hybridization with a panel of poly(A)⁻ RNA samples isolated from various adult human tissues and peripheral blood leukocytes is shown in FIG. 1. The hybridization pattern revealed three bands of approximately 1 kb, 1.7 kb, and 3.2 kb. Northern blot analysis of RNA samples isolated from leukocytes (FIG. 2) demonstrated the same pattern of multiple TPMT mRNAs in the TPMT-deficient patient, but the level of mRNA was lower when compared with that in family members with heterologous phenotypes and the two high-activity controls. These findings are consistent with the patient's mutant TPMT allele being transcribed, suggesting small alteration (e.g., point mutations, insertions, or deletions) as the molecular basis for TPMT deficiency in this patient. Moreover, Southern blotting of genomic DNA from these subjects revealed no gross differences in restriction patterns.

Cloning and Sequencing of TPMT Alleles

Figures 3A, 3B:
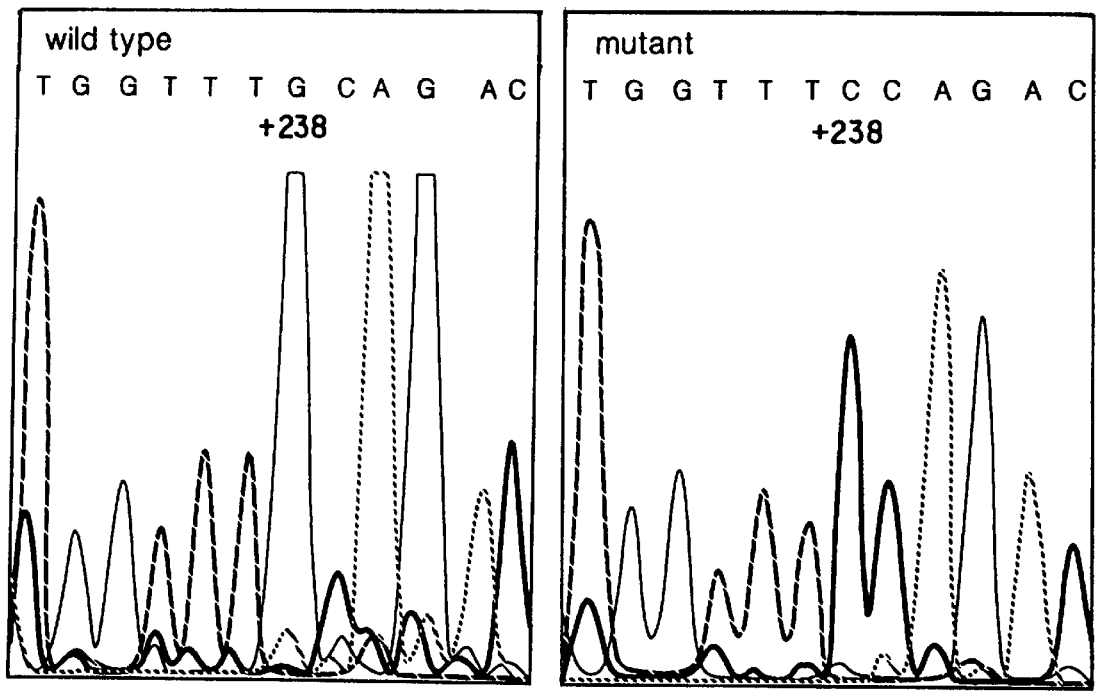
FIGS. 3A, 3B and 3C depict the difference in the TPMT wild-type and mutant sequences (SEQ ID NO:13–14).
Figure 3C:
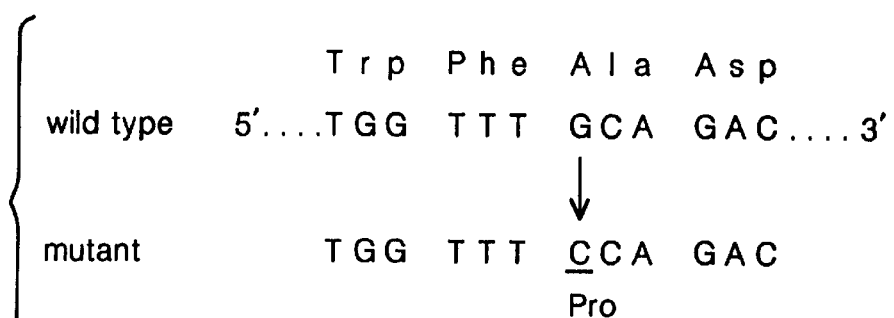

TPMT cDNA prepared from total liver RNA, as well as leukocytes from a patient with TPMT activity of 8.3 u/ml pRBC, coincided fully with the previously published sequence of the coding region of wild-type TPMT cDNA isolated from T84 colon carcinoma cells (Honchel et al., *Mol. Pharmacol.* 43:878–887 (1993)). The TPMT cDNA prepared from leukocyte RNA from the TPMT-deficient patient (Evans et al., *J. Pediatr.* 119:985–989 (1991)) revealed a single point mutation ($G^{238} \rightarrow C$) in the TPMT open reading frame, leading to an amino acid substitution ($Ala^{80} \rightarrow Pro$) in the TPMT protein encoded by this allele (FIG. 3). This was the only mutation found in four independently isolated cDNAs from this TPMT-deficient patient.

Heterologous Expression of Wild-Type and Mutant TPMT Proteins in Yeast

Figure 4A:
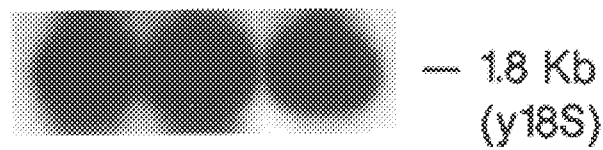
FIGS. 4A, 4B, and 4C depict Northern blot analysis of total RNA and TPMT enzymatic activity in yeast transformed with the wild-type TPMT cDNA-containing vector (left lanes), the mutant TPMT cDNA-containing vector (center lanes), and the yeast expression vector without any cDNA insert (right lanes). Each lane contained ≈20 μg of total RNA.
Figure 4B:
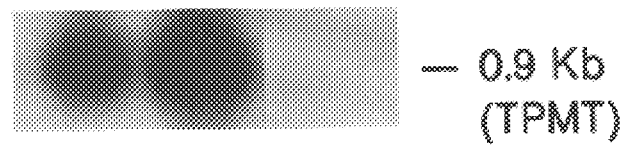
Figure 4C:
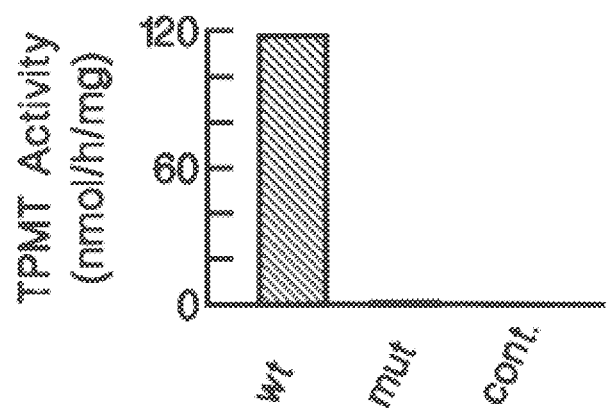

The TPMT coding region of the cDNA was reamplified by using primers 3 and 4, designed to introduce BamHI and EcoRI restriction sites at the ends of the cDNA fragment and to add an AAA sequence just before the initiation codon, to increase efficiency of expression in yeast (Krynetski et al., *Pharmacogenetics* 5:27–31 (1995)). Two recombinant plasmids were constructed that contained yeast GAL10-CYC1 promoter, either the wild-type or mutant form of TPMT cDNA, and a PGK terminator. After introduction of the vectors into the yeast cells, GAL10-CYC1 promoter was induced by galactose. Northern blot analysis demonstrated that only yeast which contained either the wild-type or the mutant TPMT cDNA synthesized TPMT mRNA, in comparable quantities (FIG. 4). Activity of the wild-type TPMT was 113–123 nmol/hr per mg of protein compared with <1.0 nmol/hr per mg of protein for mutant TPMT; no TPMT activity was found in the yeast transformed with control plasmid (i.e., no cDNA insert).

RFLP Analysis of Mutant and Wild-Type cDNA

The inactivating mutation found ($G^{238} \rightarrow C$) disrupted the recognition site of CviRI restriction endonuclease (Jin et al., Nucleic Acids Res. 22:3928–3935 (1994)), thus enabling detection of this mutation by RFLP analysis of the amplification product of the cDNA. CviRI digestion of the 232-bp PCR product obtained from wild-type cDNA by using primers 5 and 6 yielded two fragments of 116 bp, whereas the PCR product of the $G^{238} \rightarrow C$ mutant cDNA was not hydrolyzed by CviRI, as evidenced by an intact fragment of 232 base pairs. For reasons that remain unknown, the CviRI-mediated hydrolysis of the wild-type DNA fragments was incomplete, thus preventing discrimination between homozygotes and heterozygotes.

Genotype Determination

Figure 5:
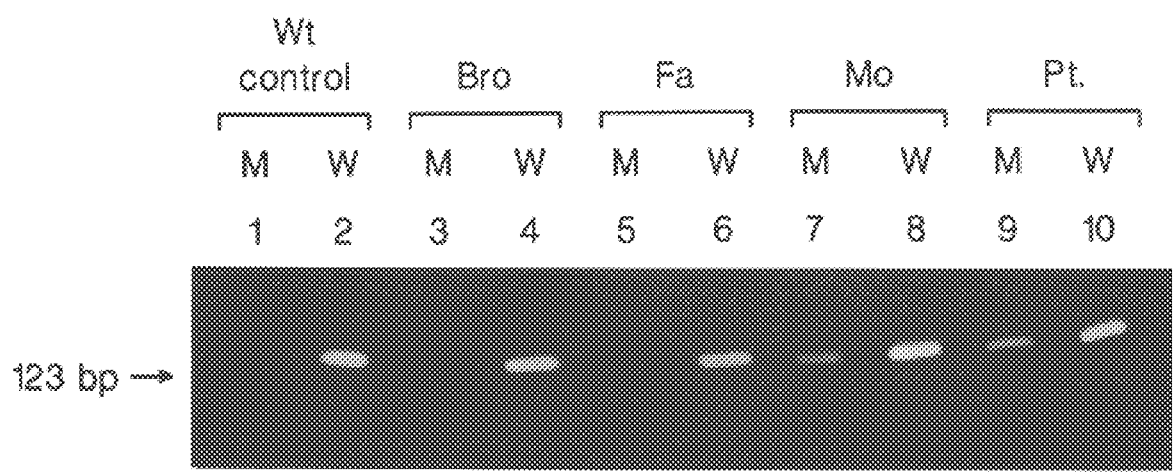
FIG. 5 depicts mutation-specific PCR amplification analysis of genomic DNA from the TPMT-deficient patient (Pt., lanes 9 and 10), her mother (Mo, lanes 7 and 8), father (Fa, lanes 5 and 6), and brother (Bro, lanes 3 and 4) and an unrelated control subject with TPMT activity of 22.8 u/ml pRBC (lanes 1 and 2). W, amplification with primers specific to wild-type genotype; M, amplification with mutant-specific primers (see Table 1 for primer sequences).

To detect the inactivating mutation in genomic DNA, a nested PCR system with mutation-specific primers was developed. Though the primary structure of the TPMT chromosomal gene is unknown, two sets of primers were designed to discriminate between the wild-type and the $G^{238} \rightarrow C$ mutant form of TPMT. The first step involved amplification of a 232-bp TPMT fragment which included nt 238 (primers 5 and 6; Table 1). The amplification product was diluted and used thereafter as a template for the second round of amplification. In the second reaction two sets of primers were used, fully coinciding with either the wild-type or the $G^{238} \rightarrow C$ mutant TPMT (see Table 1). Under the PCR conditions developed, only the perfectly matched pair of primers gave the desired 130-bp product. In this way, it was possible to detect the presence or absence of the $G^{238} \rightarrow C$ mutation in the entire family of the TPMT-deficient patient (FIG. 5). The mutation-specific PCR amplification indicated that the TPMT allele containing the inactivating $G^{238} \rightarrow C$ mutation is present in genomic DNA of the patient and her mother, but not in her father or brother. Moreover, the patient is heterozygous for $G^{238} \rightarrow C$, indicating that her other allele carries a different defect.

Discussion of Example 1

Individuals who inherit the autosomal recessive trait of TPMT deficiency develop severe hematopoietic toxicity when treated with standard dosages of mercaptopurine or azathioprine (Evans et al., J. Pediatr. 119:985–989 (1991); McLeod et al., Lancet 1341:1151 (1993); Lennard et al., Arch. Dis. Child. 69:577–579 (1993)). The majority of such patients are identified only after experiencing severe toxicity, even though prospective measurement of erythrocyte TPMT activity has been advocated by some (Lennard et al., Clin. Pharmacol. Ther. 41:18–25 (1987)). Unfortunately, TPMT assays are not widely available, and newly diagnosed patients with leukemia are frequently given erythrocyte transfusions which preclude measurement of their constitutive TPMT activity before therapy is initiated. However, the identification of the inactivating mutations of the human gene encoding TPMT has resulted in the development of PCR-based methods to determine TPMT genotype and prospectively predict phenotype, as is now done for drug-metabolizing enzymes such as debrisoquin hydroxylase (Heim and Meyer, Lancet 336:529–532 (1990)) and N-acetyltransferase (Grant, Pharmacogenetics 3:45–50 (1993)). To this end, an inactivating mutation in human TPMT has been characterized herein, with the development of a mutation-specific PCR amplification method for detecting this mutation in genomic DNA.

The nucleotide sequence of cDNA isolated from leukocyte RNA of a patient with TPMT activity of 8.3 u/ml pRBC was identical to the previously published wild-type colon carcinoma TPMT cDNA sequence. Of interest, the open reading frame of cDNA clones obtained from total liver RNA was also identical to the published wild-type colon carcinoma TPMT cDNA, which was not unexpected since TPMT activities in colon, leukocytes, and liver are correlated (Pacifici et al., Xenobiotica 23:671–679 (1993)). These results confirm the authenticity of the fragment amplified and provide the initial characterization of the human liver TPMT cDNA. Three transcripts of approximately 1.0, 1.7, and 3.2 kb were detected in all tissues evaluated (FIG. 1); the relative proportion of the 3.2-kb and 1.7-kb transcripts was found to be approximately 1:2, whereas the 1-kb transcript was consistently less abundant on Northern blots. These bands are not hybridization artifacts due to cross hybridization with rRNA, because poly(A)$^+$ RNA gave the same pattern. Since the TPMT cDNA open reading frame is only 735 bp and multiple polyadenylylation signals are present in the 3' untranslated region, these findings are not unanticipated.

When expression of TPMT mRNA was examined in the TPMT-deficient patient, Northern blot analysis of mRNA from leukocytes revealed the presence of the same-size TPMT transcripts, but at a level lower than in individuals with high TPMT activity (FIG. 2). This finding is consistent with small alterations (e.g., point mutations) as the molecular mechanism underlying the TPMT deficiency in this patient. Subsequently, 16 separate cDNA clones from four independent amplification reactions revealed $G^{238} \rightarrow C$ as the only mutation, changing codon 80 from GCA to CCA (Ala to Pro).

When the wild-type and mutant forms of the TPMT cDNA were subcloned into the yeast expression vector, wild-type and $G^{238} \rightarrow C$ mutant cDNAs produced comparable levels of hybridizable TPMT mRNA, yet the enzymatic activity of wild-type TPMT was ≈100-fold higher than that of mutant TPMT (FIG. 4). The reasons for loss of catalytic activity are unknown but could be attributed to disruption of the active site(s) or changes in the folding patterns of the protein. Proline is known to cause distortions in protein structures, suggesting that the Ala$^{80} \rightarrow$Pro substitution may result in alterations of the three-dimensional structure of the protein. According to the Chou-Fasman algorithm, the region of the protein with the Ala$\rightarrow$Pro substitution has an additional turn when compared with the wild-type TPMT protein.

To detect the $G^{238} \rightarrow C$ mutation in genomic DNA and document that this mutation was inherited by the TPMT-deficient patient, a mutation-specific PCR amplification protocol was developed and it was determined that the $G^{238} \rightarrow C$ mutation was present in genomic DNA of her mother, but not her father or brother (FIG. 5). Since one allele of the TPMT-deficient patient has a wild-type sequence at this locus, as do both alleles in her father (heterozygous phenotype), a second inactivating mutation must be present in the patient and her father. Of note, the level of mRNA expression of the second allele in the TPMT-deficient patient (if any) must be low, because multiple cDNA clones from this patient revealed only the mutant allele reported herein. Thus, additional inactivating mutations of TPMT must exist. This is not surprising, as there are multiple allelic variants responsible for other genetic polymorphisms in drug metabolism (Heim and Meyer, *Lancet 336:529–532* (1990); Grant, *Pharmacogenetics* 3:45–50 (1993)). As these additional TPMT mutations are identified, a panel of PCR-based tests has been developed to reliably predict TPMT phenotype from genotype, as is the case with debrisoquin hydroxylase (CYP2D6) and N-acetyltransferase (NAT2). Given the nature of hematopoietic toxicity when full dosages of mercaptopurine or azathioprine are given to TPMT-deficient patients (Evans et al., *J. Pediatr.* 119:985–989 (1991); McLeod et al., *Lancet* 1341:1151 (1993); Lennard et al., *Arch. Dis. Child.* 69:577–579 (1993)), which can be fatal (Schutz et al., *Lancet* 341:436 (1993)), and the inability to accurately measure TPMT activity when patients have been given erythrocyte transfusions, a reliable method to determine TPMT genotype is developed which permits the prospective identification of TPMT-deficient and heterozygous patients, so that severe toxicity can be avoided.

Total yeast RNA was extracted according to the method of Schmitt et al. (Schmitt, M. E., et al., *Nucl. Acids Res.* 18:3091 (1990)), denatured with glyoxal and dimethyl sulfoxide, electrophoresed on a 1.4% agarose gel as described (Sambrook, J., et al., *Molecular Cloning. A Laboratory Manual* 1:7.40–7.42 (1989)), and transferred to a Hybond™-N+ nylon membrane (Amersham). The wild-type human liver cDNA, cloned as described above, was labeled, with [α-$^{32}$P]dCTP using rediprime DNA labelling system (Amersham), whereas oligonucleotide y18s (5'-GGCTTGAAACCGATAGTCCCTCTAAGAAG-3' (SEQ ID NO:34), GenBank AS#J01353.Gb-Pl sequence of yeast 18S rRNA bp 1373–1401) was end labelled with [γ-$^{32}$P]ATP. Membranes were hybridized with the radiolabeled TPMT cDNA overnight, washed in sequence with 2×SSC at 65° C. for 15 min, 2×SSC containing 0.1% SDS at 65° C. for 30 min, and 0.1×SSC at 65° C. for 10 min, and exposed to x-ray film with intensifying screen at −70° C. for 6 hr to overnight. Subsequently, membranes were stripped and reprobed with y18S oligonucleotide, washed with 5×SSC 3 times at room temp for 5 min each time and finally with 5×SSC at 65° C. for 5 min, and then exposed to x-ray film with intensifying screen at −70° C. for 1 hr.

TABLE 1

Primers used for PCR amplification of the coding region of TPMT cDNA (1 and 2), site-specific mutagenesis (3 and 4), nested amplification of the wild-type allele (first round, 5 and 6; second round, 5 and 7) and the mutant allele (first round, 5 and 6; second round, 5 and 8), and for restriction fragment length polymorphism (RFLP) analysis of cDNAs (5 and 6)

| No | Sequence (5' to 3') | cDNA position |
|----|---------------------|---------------|
| 1 | GCA—CGG—AAG—ACA—TAT—GCT—TGT—GAG—AC | −44 to −19 |
| 2 | CAG—GCT—TTA—GCA—TAA—TTT—TCA—ATT—CCT—C | 779 to 806 |
| 3 | cgg—atc—caa—aAT—GGA—TGG—TAC—AAG—AAC—TTC—ACT—TGA—CAT—TG | 1 to 31 |
| 4 | cgg—aat—tcA—GGC—TTT—AGC—ATA—ATT—TTC | 787 to 805 |
| 5 | TCA—GGA—ACA—AGG—ACA—TCA—GC | 123 to 139 |
| 6 | GGT—TCC—AGG—AAT—TTC—GGT—GAT—TG | 335 to 354 |
| 7 | GTG—TCC—CCG—GTC—TGC | 238 to 252 |
| 8 | GTG—TCC—CCG—GTC—TGG | 238 to 252 |
| 9 | GCA—TTT—AGA—TAC—TTT—CCT—TAA—AGG—CA | 153 to 178 |

Positions of the primers are shown relative to the initiation ATG codon (A is in the +1 position). Non-TPMT-derived sequences are shown with lowercase letters.

EXAMPLE 2

Materials and Methods

Cloning of TPMT cDNA

Total leukocyte RNA was isolated (Chomczynski, P. and Sacchi, N., *Anal. Biochem.* 162:156 (1987)) from normal leukocytes of an 5-year-old boy with acute lymphocytic leukemia in complete remission, who had developed severe hematopoietic toxicity on standard dosages of 6MP (50 mg/m$^2$/day). At the initial presentation of toxicity, his erythrocyte concentration of TGNs was >15 fold higher than the population median (4400 versus 280 pmol/ml pRBC). Subsequently, he was documented to have TPMT-deficiency (0.6 unit/ml of packed red blood cells). First-strand cDNA was synthesized from 2 μg of total RNA and then amplified to obtain TPMT coding region as previously described (Krynetski, E. Y. et al., *Proc. Natl. Acad. Sci. (USA)* 92:949–953 (1995)). The PCR fragments were either made blunt and cloned into the Sma I site of plasmid pGEM-7Zf (+) (Promega, Madison, Wis.), or directly cloned into PCR™II (Invitrogen, San Diego, Calif.). Plasmids were purified with Qiagen kits (Qiagen, Chatsworth, Calif.) and sequenced with an automated sequencer, using the cycle sequencing reaction employing fluorescence-tagged dye terminators (PRISM, Applied Biosystems, Foster City, Calif.).

Northern Blotting

Site-directed Mutagenesis of TPMT cDNA

The wild type and mutant cDNA clones were used as templates for site-directed mutagenesis. PCR conditions were as described above except that annealing temperature was changed to 50° C. and 1.3 units of *Pyrococcus furiosus* DNA polymerase (Stratagene, La Jolla, Calif.) was used. After amplification, the PCR products were ligated into pYeDP 1/8–2 yeast expression vector as previously described (Krynetski E. Y., et al., *Proc. Natl. Acad. Sci. (USA)* 92:949–953 (1995)). In order to prepare cDNA containing either mutation found in this patient, two reverse primers were designed for further mutagenesis. The amplification was performed either with primer A (5'-cggatccaaa-ATGGATGGTACAAGAACTTCACTTGACATTG-3', 1–31) (SEQ ID NO:27) and primer B (5'-cggaattcTTACTTTTCTGTAAGTAGATATAACTTTTC-3', 709–738) (SEQ ID NO:35) using the plasmid containing mutant cDNA as the template to generate a cDNA containing only G460A (designated TPMT$_{460}$), or with primer A and C (5'cggaattcTTACTTTTCTGTAAGTAGACATAAC-TTTTC-3') (SEQ ID NO:36) using the plasmid containing wild-type cDNA as the template to generate a cDNA containing only A719G (designated TPMT$_{719}$). The resultant PCR products were also ligated into the expression vector. Recombinant plasmids were constructed that contained galactose-inducible GAL10-CYC1 promoter (Cullin, C. and Pompon, D, Gene 65:203–217 (1988)), either the wild-type or mutan forms of TPMT cDNA, and a PGK terminator. Nucleotide structures of all cDNAs were confirmed by sequencing.

Expression in Yeast Cells

Transformation of the yeast strain 2805 was carried out by treatment with lithium acetate (Becker, D. M., and Lundblad, V., Current Protocols in Molecular Biology 2:13.7.1–13.7.10 (1993)). Yeast cells transformed with recombinant expression vectors or the vector without TPMT cDNA (control) were grown on galactose-containing medium for 24 hr at 30° C. Yeast cells were treated with Lyticase (Sigma, St. Louis, Mo.), sedimented after washing with a buffer (pH 6.2) containing 20 mM 2-[N-morpholino] ethanesulfonic acid (MES) and 1.5M sorbitol, and resuspended with Tris-HCl buffer (pH 7.8) containing 100 KIU/Ml aprotinin and 1 mM phenylmethylsulfonyl fluoride. After sonication, the cytosolic fraction was obtained by centrifugation at 100,000 g for 60 min at 4° C. The concentration of protein in yeast lysates was determined using the Bio-RadDC protein assay (Lowry, O. H., et al., J. Biol. Chem. 193:265–275 (1951)). The level of expression was measured by Western blot analysis.

Western Blot Analysis of TPMT

SDS-polyacrylamide gel electrophoresis was carried out following the method of Laemmli (Laemmli, U. K., Nature 227:680–685 (1970)) using 15% acrylamide slab gels. Proteins were then electrophoretically transferred to a nitrocellulose membrane and reacted with a polyclonal rabbit antiserum against human TPMT. This antibody was produced by immunizing rabbits with GST-TPMT fusion protein (McLeod, H. L. et al., Pharmacogenetics 5 in press (1995)) and purified in sequence by affinity chromatography on sepharose with immobilized GST and GST-TPMT. The signals were visualized by enhanced chemiluminescent detection (ECL kit) following manufacturer's instructions (Amersham). TPMT content in yeast lysate expressing TPMT cDNA was estimated by this analysis using the standard of purified GST-TPMT fusion protein treated by thrombin.

TPMT Assay and Estimation of Kinetic Parameters (Vmax and Km)

Erythrocyte lysates were analyzed for TPMT activity by the non-chelated radiochemical assay of Weinshilboum and coworkers (Weinshilboum, R. M., et al., Clin. Chim. Acta 85:323–333 (1978)). For kinetic experiments, the enzymatic reaction of TPMT was carried out at 37° C. in a 1-ml mixture containing 0.1M Tris-HCl, pH 7.5, yeast cytosol expressing TPMT, various concentrations of 6MP (4 $\mu$M), and DTT (250 $\mu$M). These reaction conditions differ from that previously published (Krynetski, E. Y. et al., Mol. Pharmacol. 47:1141–1147 (1995)); i.e. incubation at 37 C instead of 21.5 C, analysis of MeMP production formation instead of substrate disappearance, and the use of higher substrate concentrations in the present study. The amount of TPMT in each reaction was made the same (0.57 $\mu$g TPMT) by adjusting the amount of yeast cytosol according to TPMT protein levels detected by the Western-blot analysis. For kinetic studies of 6MP, 1 mM of SAM was used, whereas for studies of SAM, 2 mM of 6MP was utilized. The reaction was started by the addition of yeast cytosol or 6MP (in 10 $\mu$l of DMSO), allowed to proceed for 30 min, and stopped by the addition of 100 $\mu$l M HCl. After filtration through a Centricon-3 or -10 membrane (Amicon, Inc; Beverly, Mass.), 100 $\mu$l of the filtrate was injected into HPLC to measure the formation of the methylated metabolite, MeMP, using a gradient system essentially as described in Example 1 (Krynetski, E. Y., et al., Mol. Pharmacol. 47:114–1147 (1995)).

Non-linear least-squares regression was used to estimate Vmax and Km by fitting a Michaelis-Menten model to the non-transformed data as described in Example 1 (Krynetski, E. Y., et al., Mol. Pharmacol. 47:114–1147 (1995)).

Intrinsic Stability of Recombinant TPMT Proteins

Yeast cytosols expressing wild-type $TPMT_{460}$, or $TPMT_{719}$ protein were incubated in 0.1M Tris-HCl (pH 7.5) at 37° C. (after an equilibration time of 3 min from 0° C. to 37° C.) for different lengths of time before being added to an assay mixture similar to that described above except using fixed concentrations of 2 mM 6MP and 1 mM SAM. The assay of TPMT activity was then allowed to proceed for 15 min at 37° C., and MeMP was measured as described above. Total protein concentrations of yeast lysate in the incubation mixture were 0.09, 0.37, 0.08 mg/ml for the wild-type, $TPMT_{460}$, and $TPMT_{719}$, respectively, to give equal amount of TPMT in the incubation. The same assay mixture without yeast lysate served as the blank, and the background values for non-enzymatic methylation (<10%) were subtracted from all values obtained. An aliquot of sample at each time point was taken for Western blot analysis. The samples at 0° C., 0 hr served as controls for the blots with $TPMT_{460}$ and $TPMT_{719}$.

RFLP Analysis to Detect Mutation in cDNA

TPMT cDNA synthesized by reverse transcription-PCR was used as a template in PCR amplifications with primer D (5'-CAGGCTTTAGCATAATTTTCAATTCCTC-3', 779–806) (SEQ ID NO:26) and primer E (5'-CAGAAGAACCAATCACCG-3', 323–340) (SEQ ID NO:37), for 30 cycles of denaturation at 94° C. for 1 min, annealing at 50° C. for 45 sec, and elongation at 72° C. for 1.5 min. The synthesized DNA fragments were digested with AccI and MwoI restriction endonuclease (New England Biolabs, Beverly, Mass.) and analyzed by 2.5% MetaPhor agarose (FMC, Rockland, Me.). Digestion of wild-type DNA fragments by MwoI yields two fragments (340 bp and 144 bp), while the A460G mutation eliminates the MwoI restriction site, yielding one fragment of 384 bp). Alternatively, the G719A mutation adds an AccI restriction site, yielding two fragments (398 bp and 86 bp) when the mutation is present, but only one fragment with the wild-type sequence.

Detection of A460G Mutation of the TPMTB Allele in Genomic DNA 250 ng of patient's DNA was used as template in PCR assay using primer A (ATG TAA TAC GAC TCA CTA TAA CCT GGA TTA ATG GCA AC, 466–483) (SEQ ID NO:38) and primer B (ATA ACA GAG TGG GGA GGC TGC, 408–428 of intron sequence) (SEQ ID NO:10) in buffer A (Invitrogen, San Diego, Calif.) containing 60 mM tris-HCl pH 8.5, 15 mM ammonium sulfate, 1.5 mM $MgCl_2$. Amplification conditions were: cycle 1, 80° C.—for 1 min, 94° C. for 2 min. 5 $\mu$l of 10 mM dNTP were added after heating to 80° C. ("Hot start" protocol). The reaction proceeded at 94° C. for 1 min, 55° C. for 2 min and 72° C. for 1 min for 35 cycles more and was accomplished with incubation for 7 min at 72° C. The products of the reaction were digested with MwoI restriction endonuclease (New England Biolabs, Beverly, Mass.) according to manufacturer's instructions and analyzed by electrophoresis in 2.5% Metaphor agarose (FMC, Rockland, Me.). 123 bp DNA Ladder length markers (GIBCO, Gaithersburg, Md.) were used to estimate the fragments' size. MwoI digestion of wild-type DNA yielded a fragment of 265 bp, whereas DNA containing the A460G mutation was not digested, yielding a fragment of 303 bp.

Data Analysis

The University of Wisconsin Genetics Computer Group software package was used to analyze sequence information (Genetic Computer Group, *Program Manual for the GCG Package, Version* 7(1991)). A two-tailed t-test was used to determine whether the model parameter estimates for Vmax and Km differed significantly from 0. Multiple comparison procedure utilizing Bonferroni adjustment was used to identify differences between kinetic parameters of the wild-type or mutant TPMTs expressed in yeast.

Results

Cloning and Sequencing of TPMT Alleles

Figure 6A:
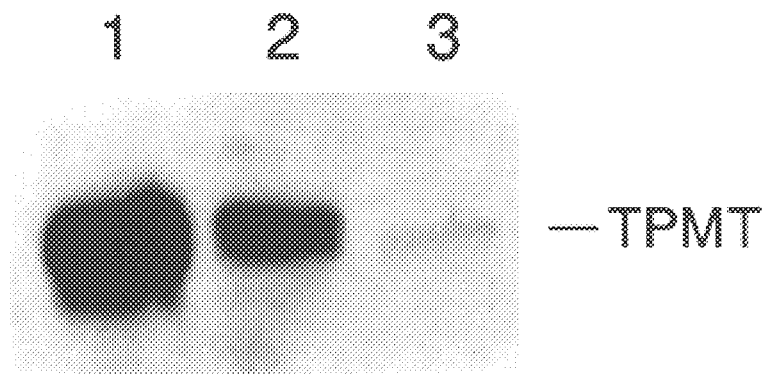
FIGS. 6A and 6B depict relative level of TPMT protein and activity in a wild-type and a deficient patient.
Figure 6B:
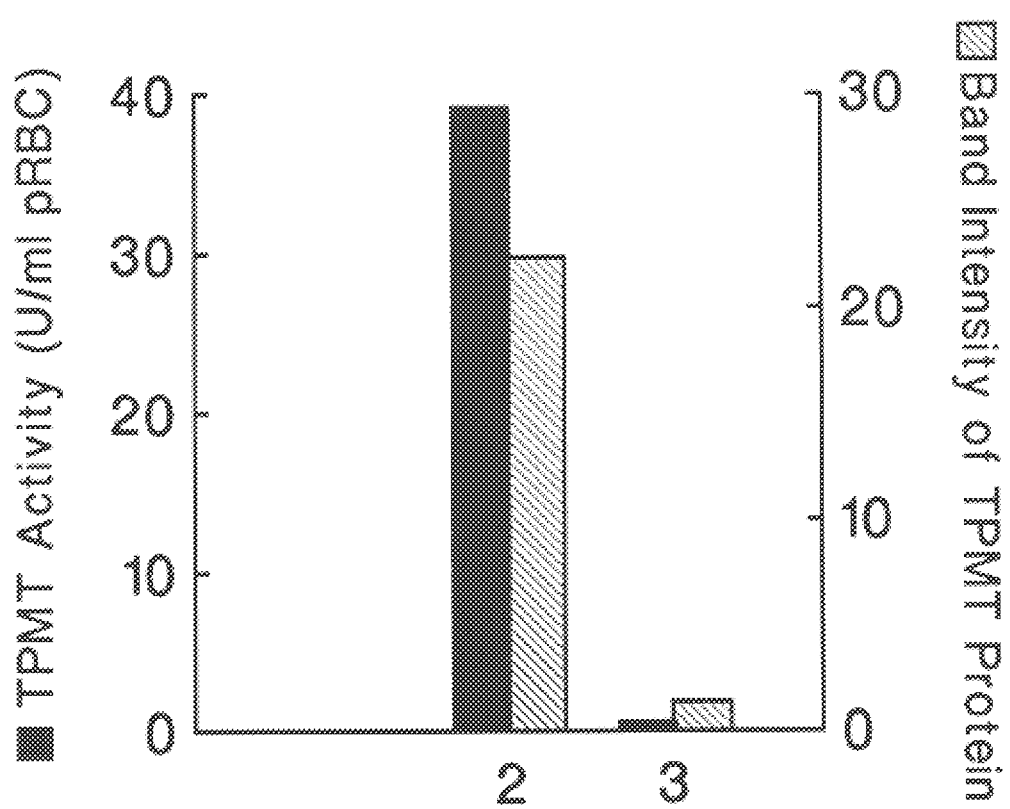

First-strand cDNA was synthesized from total RNA of a TPMT-deficient patient whose erythrocyte TPMT activity and protein levels were 20–30 fold less than wild-type patients (FIG. 6), and clones containing the TPMT open-reading frame were obtained from six independent PCR reactions. These clones were sequenced and revealed two distinct cDNAs, nine clones each. One sequence contained only the point mutation $G^{238} \rightarrow C$, described above, a mutant allele designated TPMTA. The other sequence (FIG. 7) contained two point mutations, $G^{460} \rightarrow A$ (G460A) and $A^{719} \rightarrow G$ (A719G), leading to amino acid substitutions at codon 154 ($Ala^{154} \rightarrow Thr$) and codon 249 ($Tyr^{240} \rightarrow Cys$), designated TPMTB. The equal abundance of cDNA clones for these two sequences suggests they are from two alleles of the TPMT gene expressed at comparable levels in this patient.

Detection of TPMTB in Propositus Family Members

After restriction mapping of the TPMTB allele, G460A was found to eliminate the recognition site of MwoI, while A719G added an AccI restriction site. Based on these findings, restriction fragment length polymorphism was used to identify the TPMTB allele in the propositus and his family members. The wild-type cDNA was cut by MwoI, but not by AccI, whereas the deficient patient's cDNA was heterozygous with respect to these restriction sites (FIG. 8), consistent with this patient having two different mutant TPMT alleles (i.e. TPMTA and TPMTB). Furthermore, the mother's TPMTB restriction pattern was the same as the propositus, while the father did not have the TPMTB allele, indicating that this patient inherited the TPMTB allele from his mother.

Heterologous Expression of the Wild-type and Mutant TPMT

Figure 9A:
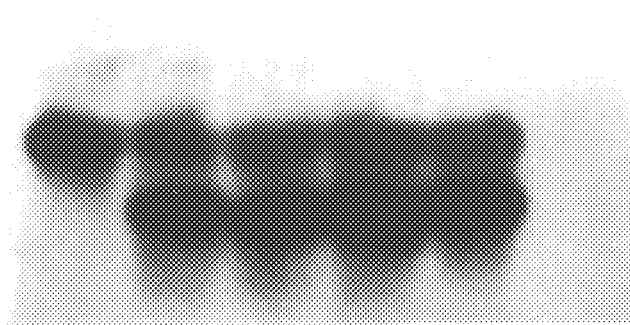
FIGS. 9A, 9B, and 9C depict comparison of TPMT mRNA, protein, and activity levels in yeast transformed with vector alone without any insert (lane 1), vector with wild-type cDNA (lane 2), vector with cDNA containing G460A (lane 3), vector with cDNA containing A719G (lane 4), vector with cDNA containing both G460A and A719G (TPMTB) (lanes 5 and 6).
Figure 9B:
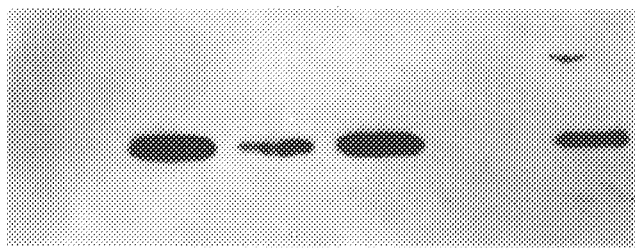
Figure 9C:
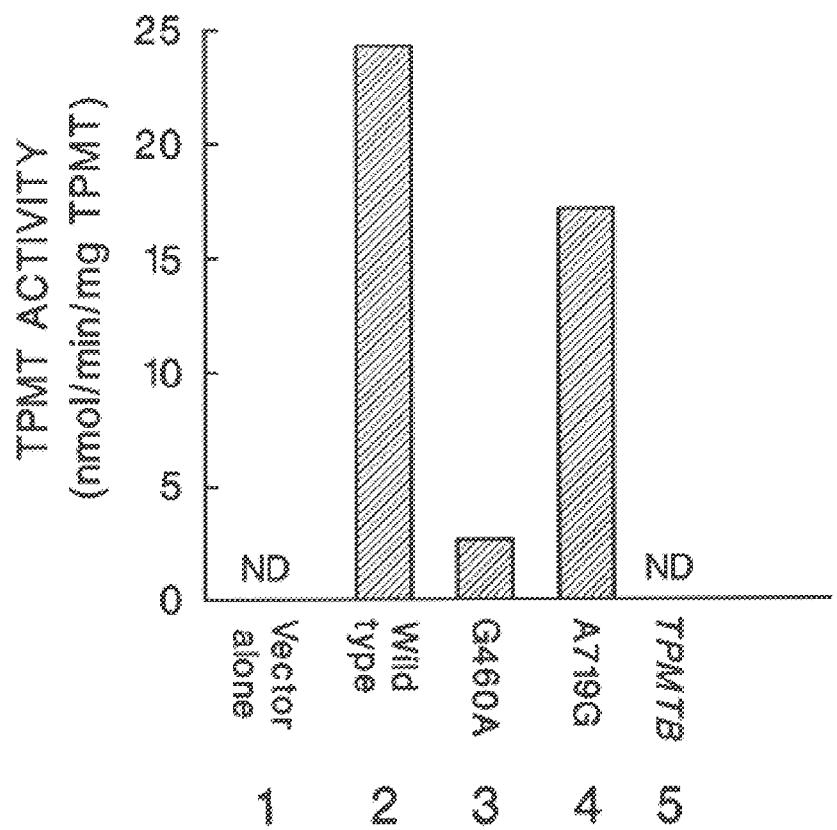

As shown in FIG. 9A, the TPMT mRNA levels were similar in yeast expressing the wild-type and each of the three mutant cDNAs (i.e. $TPMT_{460}$ with only the G460A, $TPMT_{719}$ with only the A719G, and TPMTB with both mutations), suggesting that either of the point mutations alone or in combination did not alter transcription of TPMT cDNAs. TPMT mRNA was not detected with yeast expressing the vector alone. In contrast, TPMT protein levels were similar between the wild-type and the $TPMT_{719}$ mutant cDNA, but protein levels for the $TPMT_{460}$ and TPMTB were 4-fold and 400-fold less than the wild-type, respectively (FIG. 9B). TPMTB protein was detectable only when 100-fold more of yeast lysate protein was loaded on the gel (FIG. 9B, lane 6), whereas no protein binding to anti-TPMT-specific antibodies was detected with yeast expressing vector without cDNA (FIG. 9B), even with loading 150-fold more of the yeast lysate (36 μg). Thus, neither point mutation alone altered TPMT protein levels comparable to the cDNA with both mutations. In addition, when activity was normalized to the TPMT content in yeast lysates and compared with wild-type, the catalytic activity of $TPMT_{460}$ was reduced to a greater extent (9-fold) than that of $TPMT_{719}$ (1.4-fold), whereas no activity of TPMTB could be detected even at 6MP concentrations up to 2 mM.

Michaelis-Menten Kinetic Constant for S-methylation

While TPMT activity was undetectable with TPMTB, the modest activity of mutant $TPMT_{460}$ and $TPMT_{719}$ permitted estimation of kinetic parameters for both 6MP and SAM as substrates. Table 2 summarizes Vmax and Km values for 6MP or SAM, estimated by fitting a Michaelis-Menten model to the untransformed data. All parameter estimates were significant at p<0.05 (two tailed t-test). Both Km and Vmax values for 6MP or SAM were significantly higher (p<0.01) for $TPMT_{460}$ compared to wild-type, while Vmax and Km for $TPMT_{719}$ were not significantly different from the wild-type (Table 2). Therefore, the intrinsic clearance (i.e. Vmax/Km) for $TPMT_{460}$ was 13-fold lower than wild-type, while $TPMT_{719}$ was comparable to wild-type.

Stability of Recombinant TPMT Proteins in vitro

Figure 10A:
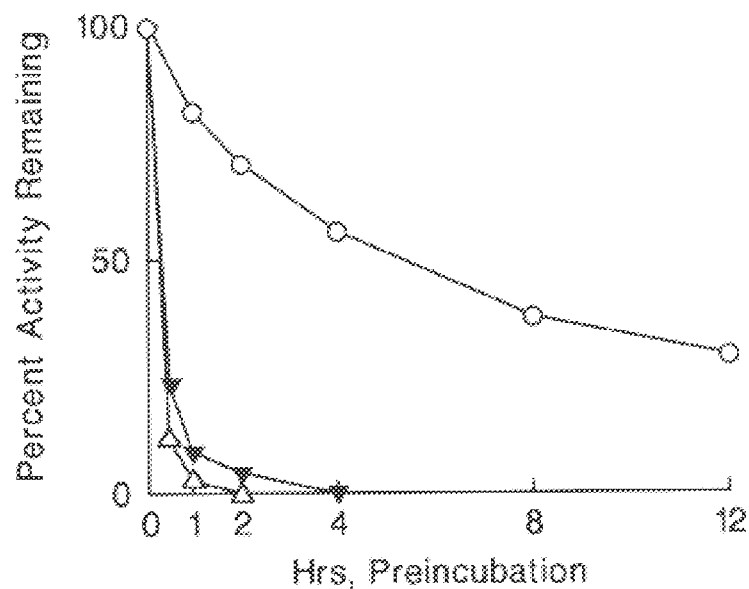
FIGS. 10A, 10B, 10C, and 10D depict in vitro stabilities of TPMT wild-type and mutant proteins.
Figure 10B:
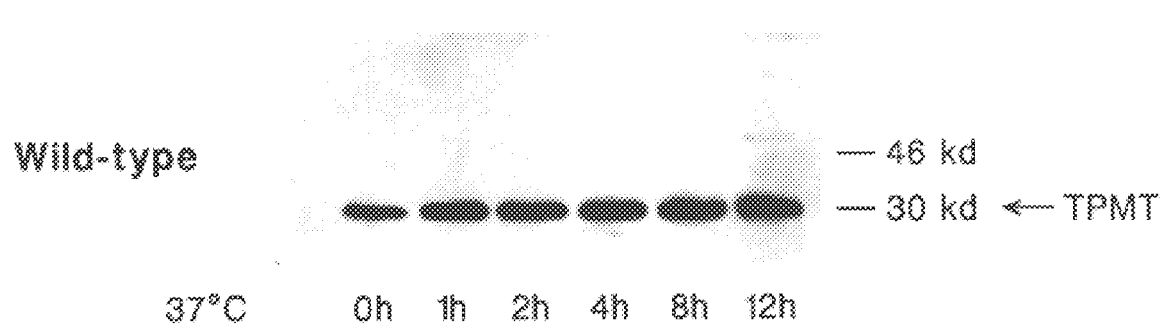
Figure 10C:
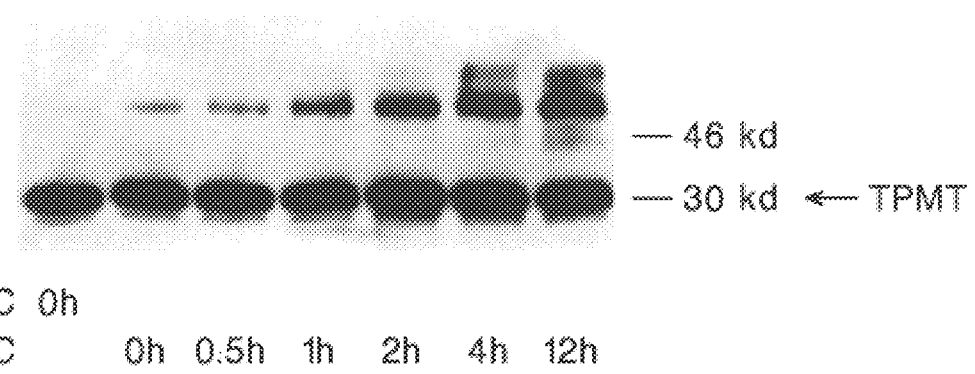
Figure 10D:
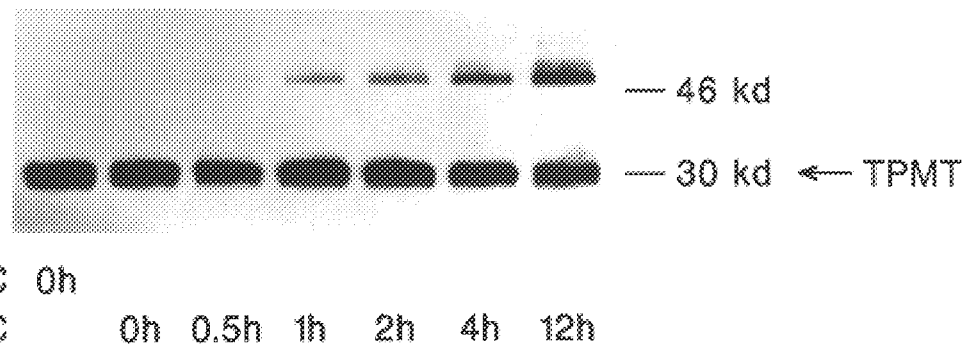

As shown in FIG. 10A, both $TPMT_{460}$ and $TPMT_{719}$ proteins were rapidly inactivated at 37° C. (within 4 hr), while 30% of the wild-type TPMT activity remained at 12 hr under the same conditions. Western blot analysis (FIGS. 10B–10D) shows that under these conditions TPMT protein content did not change substantially for the wild-type or mutants, suggesting that the reduction in activity for mutants largely reflects intrinsic instability, not degradation of the protein. Interestingly, a higher molecular weight (≈52 kd) protein band recognized by anti-TPMT antibody, increased in a time-dependent manner. This band, presently of unknown identity, was not evident for the wild-type until 12 hr of incubation; in contrast, this band appeared immediately (after 3 min warm-up from 0° C. to 37° C.) for $TPMT_{460}$ and within 30 min for $TPMT_{719}$.

Discussion of Example 2

The major mutant allele associated with thiopurine S-methyltransferase deficiency in humans, an autosomal recessive trait that can have fatal consequences (Shutz, E., et al., *Lancet* 341:436 (1993)) was identified and described herein, i.e. in Example 2. Initially, an inactivating point mutation at the human TPMT locus (G238C) described in Example 1 (Krynetski, E. Y., et al., *Proc. Natl. Acad. Sci.* (USA) 92:949–953 (1995)), was identified. This allele (TPMTA) comprises only a small percentage of TPMT mutations.

Further investigation identified the most prevalent mutant allele (TPMTB) associated with human TPMT-deficiency in Caucasians, comprising about 70% of mutant alleles in this population. The deficient patient from whom this allele was isolated had TPMT protein and activity levels 20–30 fold less than individuals with wild-type phenotypes (FIG. 6), indicating that his TPMT-deficiency was due to low levels of TPMT protein. This is consistent with previous immunotitration studies demonstrating that the immunoreactive protein of TPMT is correlated with enzymatic activity (Woodson, L. C., et al., *J. Pharmacol. Exp. Ther.* 222:174–181 (1982)). The residual TPMT protein in this patient may be from his TPMTA allele, which is associated with a 20-fold reduction in TPMT protein when expressed in yeast.

Heterologous expression of the TPMTB cDNA in yeast produced TPMT mRNA levels comparable to wild-type, indicating that these mutations have no significant impact on transcription in yeast. However, the TPMT protein level was about 400-fold less in yeast expressing TPMTB compared to the wild-type cDNA, indicating a posttranscriptional mechanism for the loss of TPMT activity. The TPMTB cDNA contains two transition mutations (G460A and A719G), which differ from the single nucleotide transversion responsible for loss of activity in the TPMTA cDNA described above (Krynetski, E. Y., et al., *Proc. Natl. Acad. Sci.* (*USA*) 92:949–953 (1995)). To determine the relative contribution of the two point mutations in TPMTB, site-directed mutagenesis was used to generate mutant cDNAs with either G460A mutation (TPMT$_{460}$) or the A719G mutation (TPMT$_{719}$). When expressed in yeast, TPMT mRNA levels were comparable for wild-type, TPMTB, TPMT$_{460}$, and TPMT$_{719}$ (FIG. 9A). However, TPMT protein levels were 4-fold lower for TPMT$_{460}$ and about 400-fold lower for TPMTB, compared to wild-type, while TPMT$_{719}$ had protein levels comparable to wild-type (FIG. 9A). These data suggest that the presence of either the G460A or A719G transitions alone has only modest (G460A) or no effect (A719G) on translation, while the presence of both mutations leads to a marked reduction in TPMT protein. Furthermore, there was instability of TPMT catalytic activity conferred by either point mutation alone, in vitro (FIG. 10), and no detectable activity when both mutations were present. As depicted in FIG. 10, a higher molecular weight protein recognized by an anti-TPMT antibody, accumulates during in vitro incubation of recombinant proteins, particularly noteworthy with the mutant cDNAs. While the identity of the 52 kd band is unknown, it could represent the formation of a multiubiquitin chain attached to the unfolded TPMT protein (Ciechanover, A. and Schwartz, A. L., *FASEB J.* 8:182–191 (1994)).

In addition to changes in stability of TPMT activity, the G460A transition was associated with a marked increase in Km for both 6MP (46-fold) and the co-substrate SAM (200-fold, such that the intrinsic clearance for 6MP methylation (Vmax/Km) was >10-fold lower than wild-type protein. Of note, the Vmax/Km ratio for heterologously expressed TPMTA, described above (Krynetski, E. Y. et al., *Proc. Natl. Acad. Sci.* (*USA*) 92:949–953 (1995)), was 5-fold lower than wild-type TPMT. While stability of the mutant proteins was a concern for the present experiments, the kinetic parameters for TPMT$_{460}$ and TPMT$_{719}$ were substantially different from each other, despite similar protein stability.

Using mutation-specific PCR-RFLP analysis, the G460A transition was found in genomic DNA from 18 of 25 unrelated individuals with heterozygous TPMT phenotypes. Thus, the TPMTB allele comprised 72% of mutant TPMT alleles in this population, indicating that it is the predominant mutation in Caucasians. Of note, an unrelated TPMT-deficient patient, previously described (McLeod, H. L., et al., *Lancet* 341:1151 (1993)) has now been identified as homozygous for the TPMTB allele, by cDNA sequencing and by the PCR-RFLP method described herein. Thus, TPMT-deficient patients with either TPMTA/TPMTB, or TPMTB/TPMTB genotypes have now been documented. While additional TPMT mutations will likely be discovered, the present investigation has identified the major mutant allele at the human TPMT locus in Caucasians. Given the importance of 6MP for curative therapy of acute lymphoblastic leukemia and the evolving role of azathioprine immunosuppression for organ transplantation (Hollander et al., *Lancet* 345:610–614 (1995)), the DNA-base method of the present invention for prospectively diagnosing TPMT-deficiency should minimize the risk of potentially life-threatening hematopoietic toxicity in these patients.

TABLE 2

Kinetic parameters$^§$ of substrate (6MP) and co-substrate (SAM) for S-methylation of 6-MP catalyzed by human TPMT cDNAs expressed in yeast

| cDNA Expressed | KM ($\mu$M) | Vmax (nmol/min/mg TPMT) | Vmax/Km (ml/min/mg TPMT) |
|---|---|---|---|
| 6MP: | | | |
| wild-type | 95.3 ± 5.5 | 260.6 ± 9.8 | 2.7 |
| TPMT$_{460}$ | 4396 ± 1367 | 958.5 ± 187.9 | 0.2 |
| TPMT$_{719}$ | 182.5 ± 10.1 | 338.8 ± 13.5 | 1.9 |
| TPMTB | ND | ND | |
| SAM: | | | |
| wild-type | 6.6 ± 1.1 | 173.1 ± 14.1 | 26.2 |
| TPMT$_{460}$ | 1375 ± 211 | 704.9 ± 69.7 | 0.51 |
| TPMT$_{719}$ | 9.5 ± 1.4 | 226.9 ± 19.1 | 23.9 |
| TPMTB | ND | ND | |

$^§$Kinetic parameters for 6MP were estimated using 1 mM SAM in the assays; and parameters for SAM were estimated at 2 mM 6MP. All values are expressed as mean ± SE.
ND = activity not detectable While the foregoing invention has been described in some detail for purposes of clarity and understanding, it will be appreciated by one skilled in the art from a reading of this disclosure that various changes in form and detail can be made without departing from the true scope of the invention and appended claims. All patents and publications mentioned herein are incorporated by reference in their entirety.

What is claimed is:

1. An isolated polynucleotide molecule comprising a mutant allele of thiopurine S-methyltransferase (TPMT) or a fragment thereof, which is at least ten consecutive bases long and contains a point mutation at cDNA position 238.

2. An isolated polynucleotide molecule as claimed in claim 1, wherein said point mutation is a cytosine substitution for guanine.

3. An isolated polynucleotide molecule as claimed in claim 2, wherein said polynucleotide molecule has the sequence shown in FIG. 11 (SEQ ID NO:1).

4. An isolated polynucleotide molecule comprising a mutant allele of thiopurine S-methyltransferase (TPMT) or a fragment thereof, which is at least ten consecutive bases long and contains a point mutation at cDNA position 460.

5. An isolated polynucleotide molecule as claimed in claim 4, wherein said point mutation is an adenine substitution for guanine.

6. An isolated polynucleotide molecule as claimed in claim 5, wherein said polynucleotide molecule has the sequence shown in FIG. 12 (SEQ ID NO:3).

7. An isolated polynucleotide molecule comprising a mutant allele of thiopurine S-methyltransferase (TPMT) or a fragment thereof, which is at least ten consecutive bases long and contains a point mutation at cDNA position 719.

8. An isolated polynucleotide molecule as claimed in claim 7, wherein said point mutation is a guanine substitution for adenine.

9. An isolated polynucleotide molecule as claimed in claim 8, wherein said polynucleotide molecule has the sequence shown in FIG. 13 (SEQ ID NO:5).

10. An isolated polynucleotide molecule comprising a mutant allele of thiopurine S-methyltransferase (TPMT) or a fragment thereof, which is at least 260 consecutive bases long and contains a point mutation at cDNA position 460 and a point mutation at cDNA position 719.

11. An isolated polynucleotide molecule as claimed in claim 10, wherein the point mutation at position 460 is an adenine substitution for guanine and the point mutation at position 719 is a guanine substitution for adenine.

12. An isolated polynucleotide molecule as claimed in claim 11, wherein said polynucleotide molecule has the sequence shown in FIG. 14 (SEQ ID NO:7).

13. An isolated polynucleotide molecule fully complementary to any one of the polynucleotide molecules identified as SEQ ID NOS:1, 3, 5, or 7 or a fragment thereof, wherein said fragment is at least 10 bases long and contains at least one point mutation selected from the group consisting of G283C, G460A, and A719G.

14. A diagnostic assay for determining thiopurine S-methyl-transferase (TPMT) genotype of a subject which comprises (a) isolating nucleic acid from said subject;
(b) amplifying a thiopurine S-methyltransferase (TPMT) PCR fragment from said nucleic acid, which includes at least one of cDNA positions 238, 460, or 719, thereby obtaining an amplified fragment; and
(c) sequencing the amplified fragment obtained in step (b), thereby determining the thiopurine S-methyltransferase (TPMT) genotype of said subject.

15. A diagnostic assay for determining thiopurine S-methyl-transferase (TPMT) genotype of a subject which comprises (a) isolating nucleic acid from said subject;
(b) amplifying a thiopurine S-methyltransferase (TPMT) PCR fragment from said nucleic acid using a first and a second set of primers in a first and a second PCR reaction, respectively; wherein the first set of primers contains primer X and primer Y, and the second set of primers contains primer X and primer Z; wherein
  (i) the Y primer is complementary to a region 5' to one of three point mutation sites at cDNA positions 238, 460, or 719, and includes the wild type nucleotide for said cDNA position;
  (ii) the Z primer is identical to the Y primer except that instead of the wild type nucleotide, it contains the respective mutant nucleotide at the respective cDNA positions 238, 460, or 719; and
  (iii) the X primer is complementary to a region 3' to the point mutation site corresponding to primers Y and Z;
(c) amplifying the sequence in between primers X and Y and in between primers X and Z; thereby obtaining an amplified fragment in each of the first and the second PCR reactions; and
(d) visualizing the contents of the first and the second PCR reactions, thereby determining the thiopurine S-methyltransferase (TPMT) genotype of said subject.

16. A diagnostic assay for determining thiopurine S-methyl-transferase (TPMT) genotype of a subject which comprises (a) isolating nucleic acid from said subject;
(b) amplifying a thiopurine S-methyltransferase (TPMT) PCR fragment from said nucleic acid, which includes at least one of cDNA positions 238, 460, or 719, thereby obtaining an amplified fragment; and
(c) treating the amplified DNA fragment obtained in step (b) with
  (i) CviRI in its corresponding restriction buffer to detect presence or absence of a point mutation at cDNA position 238,
  (ii) MwoI in its corresponding restriction buffer to detect presence or absence of a point mutation at cDNA position 460, or (iii) AccI in its corresponding restriction buffer to detect presence or absence of a point mutation at cDNA position 719, thereby determining the thiopurine S-methyltransferase (TPMT) genotype of said subject.

17. A diagnostic assay as claimed in claim 16, further comprising (b') amplifying cDNA, which is wild-type for TPMT sequence, for a wild-type TPMT fragment, thereby obtaining a wild-type TPMT fragment; and (c') treating the wild-type TPMT fragment obtained in step (b') with CviRI in its corresponding restriction buffer, MwoI in its corresponding restriction buffer, or AccI in its corresponding restriction buffer;

wherein steps (b') and (c') are performed as controls in parallel with steps (b) and (c).

18. A diagnostic assay for determining thiopurine S-methyl-transferase (TPMT) genotype of a subject which comprises (a) isolating nucleic acid from said subject;

(b) making a first and a second PCR primer wherein
(i) the first PCR primer is complementary to a region 5' to one of three point mutation sites at cDNA positions 238, 460, or 719; and
(ii) the second PCR primer is complementary to a region 3' to the same one of the three point mutation sites at cDNA positions 238, 460, or 719;

(c) amplifying the sequence in between the first and the second primers; thereby obtaining an amplified fragment; and (d) treating the amplified fragment obtained in step (c) with (i) CviRI in its corresponding restriction buffer to detect presence or absence of a point mutation at cDNA position 238, (ii) MwoI in its corresponding restriction buffer to detect presence or absence of a point mutation at cDNA position 460, or (iii) AccI in its corresponding restriction buffer to detect presence or absence of a point mutation at cDNA position 719, thereby determining the thiopurine S-methyltransferase (TPMT) genotype of said subject.

19. A diagnostic kit for determining thiopurine S-methyltransferase (TPMT) genotype of a subject comprising a carrier means having in close confinement therein at least two container means, wherein a first container means contains a first polynucleotide molecule as claimed in claims 2, 5, 8, or 11, or a polynucleotide molecule complementary thereto and a second container means contains a second polynucleotide molecule encoding a wild-type allele of thiopurine S-methyltransferase (TPMT), a fragment thereof, or a polynucleotide molecule complementary thereto which is ten consecutive bases long and contains at least one of cDNA positions 238, 460, or 719, corresponding to the first polynucleotide of the first container means.

20. An isolated polynucleotide molecule having a sequence shown in FIG. 15 (SEQ ID NO:9) or a fragment thereof which is at least ten bases long.

21. An isolated polynucleotide molecule as claimed in claim 20, wherein the polynucleotide molecule has the nucleotide sequence identified as SEQ ID NO:10.

22. An isolated polynucleotide molecule fully complementary to the polynucleotide claimed in claim 20.

* * * * *

UNITED STATES PATENT AND TRADEMARK OFFICE
CERTIFICATE OF CORRECTION

PATENT NO. : 5,856,095

DATED : January 5, 1999

INVENTORS : Evans et al.

It is certified that an error appears in the above-identified patent and that said Letters Patent is hereby corrected as shown below.

Column 3, line 15, please delete "FIG. 11" and insert therein --Figures 11A-11B--.

Column 3, line 17, please delete "FIG. 12" and insert therein --Figures 12A-12B--.

Column 3, line 20, please delete "FIG. 13" and insert therein --Figures 13A-13B--.

Column 3, line 30, please delete "FIG. 14" and insert therein --Figures 14A-14B--.

Column 5, line 31, please delete "(FIG. 3A)" and insert therein --(Figures 3A-3B)--.

Column 5, line 35, please delete "(FIG. 3B)" and insert therein --(Figures 3C)--.

Figure 7A:
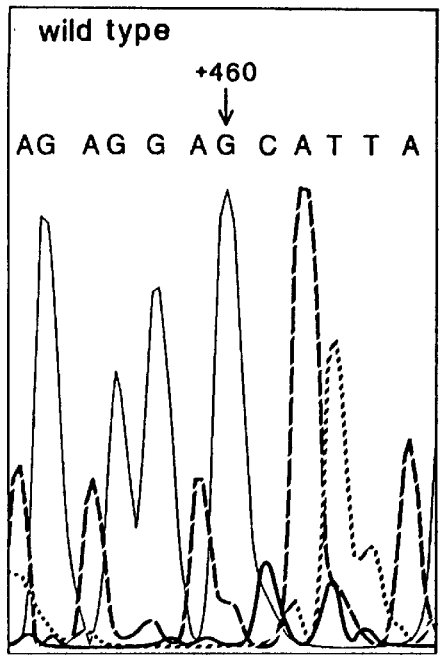
FIGS. 7A–7F depict differences in the wild-type (SEQ ID NO:15–18) and mutant (SEQ ID NO:19–22) TPMT cDNA sequence and deduced amino acid sequence of the protein encoded. Two segments of the sequences are displayed.
Figure 7B:
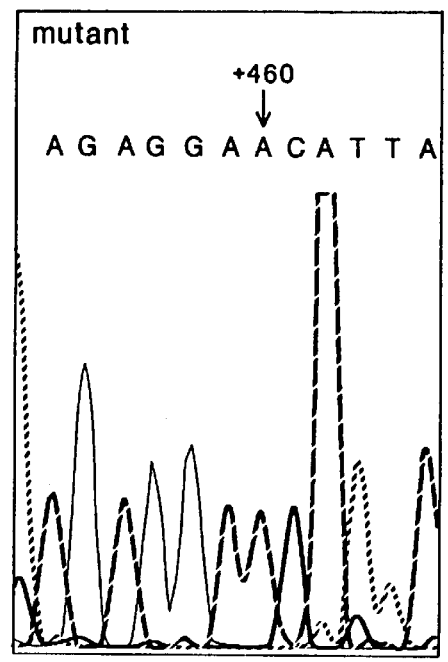
Figure 7C:
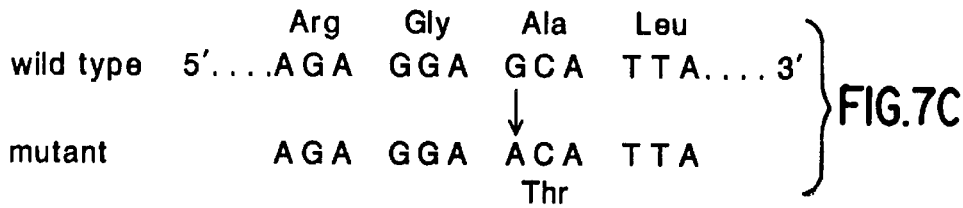

Column 6, line 4-5, please delete "FIG. 7A depicts" and insert therein --Figures 7A-7C depict--.

Figure 7D:
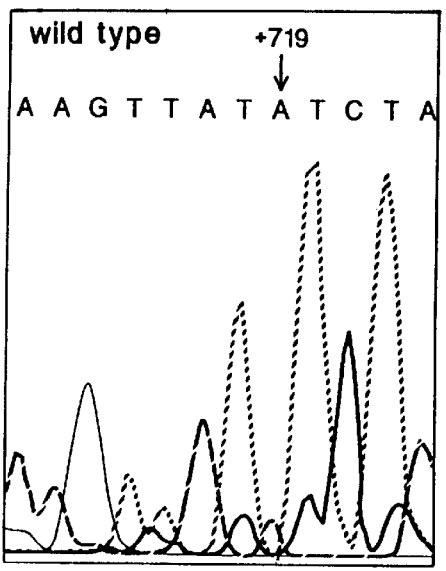
Figure 7E:
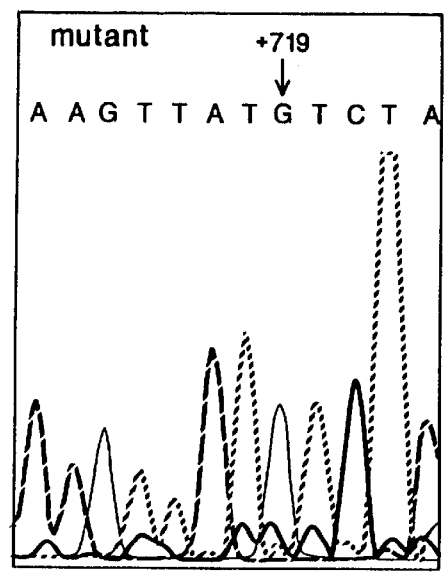
Figure 7F:
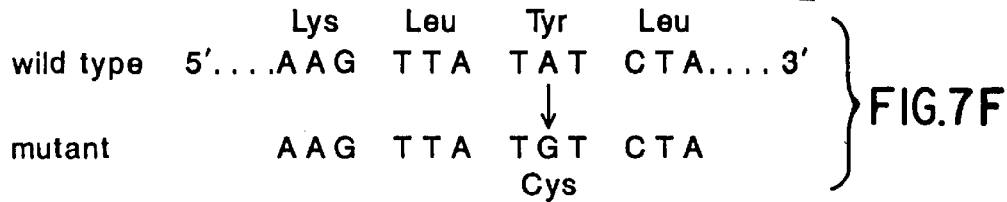
Figure 8A:
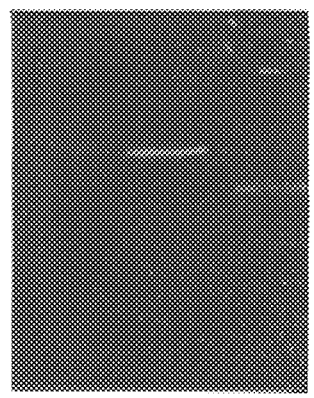
FIGS. 8A, 8B, 8C, and 8D depict PCR-RFLP analysis of cDNAs from the patient and his family members. A wild-type cDNA was included as the control. Three samples were run for each cDNA, a cDNA fragment (nucleotide 323–806, 484 bp) amplified by PCR without restriction enzyme digestion (lane 1), PCR products digested by AccI to yield 398 bp and 86 bp fragments when the G719A mutation was present (lane 2), PCR products digested by MwoI to yield 340 bp and 144 bp fragments when the wild-type sequence was present at nucleotide 460 or one fragment of 484 bp when the G460A mutation was present (lane 3), and a 123 bp DNA ladder (lane M).
Figure 8B:
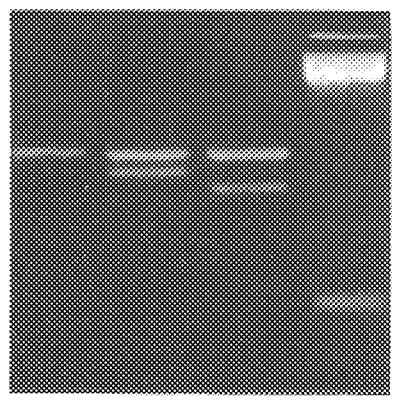
Figure 8C:
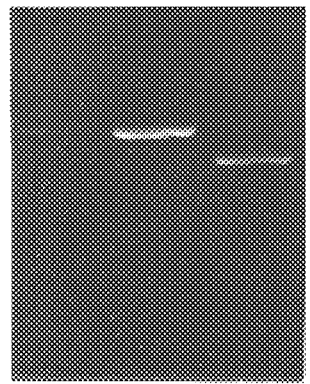
Figure 8D:
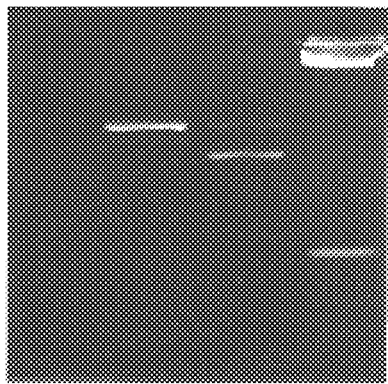

Column 6, line 5, please delete "FIG. 7B depicts" and insert therein --Figures 7D-7F depict--.

Column 6, line 46, please delete "FIG. 11 depicts" and insert therein --Figures 11A-11B depict--.

Column 6, line 49, please delete "FIG. 12 depicts" and insert therein --Figures 12A-12B depict--.

UNITED STATES PATENT AND TRADEMARK OFFICE
CERTIFICATE OF CORRECTION

PATENT NO. : 5,856,095

DATED : January 5, 1999

INVENTORS : Evans *et al.*

It is certified that an error appears in the above-identified patent and that said Letters Patent is hereby corrected as shown below.

Column 6, line 51, please delete "FIG. 13 depicts" and insert therein --Figures 13A-13B depict--.

Column 6, line 53, please delete "FIG. 14 depicts" and insert therein --Figures 14A-14B depict--.

Column 14, line 58, please delete "(FIG. 3)" and insert therein --(Figures 3A-3C)--.

Column 15, line 8, please delete "(FIG. 4)" and insert therein --(Figures 4A-4C)--.

Column 16, line 36, please delete "(FIG. 2)" and insert therein --(Figures 2A-2C)--.

Column 21, line 16, please delete "(FIG. 6)" and insert therein --(Figures 6A-6B)--.

Column 21, line 21, please delete "(FIG. 7)" and insert therein --(Figures 7A-7F)--.

Column 21, line 37, please delete "(FIG. 8)" and insert therein --(Figures 8A-8D)--.

Column 22, line 50, please delete "(FIG. 6)" and insert therein --(Figures 6A-6B)--.

Column 23, line 19-20, please delete "(FIG. 10)" and insert therein --(Figures 10A-10D)--.

Column 23, line 21, please delete "FIG. 10" and insert therein --Figures 10A-10D--.

UNITED STATES PATENT AND TRADEMARK OFFICE
CERTIFICATE OF CORRECTION

PATENT NO. : 5,856,095

DATED : January 5, 1999

INVENTORS : Evans et al.

It is certified that an error appears in the above-identified patent and that said Letters Patent is hereby corrected as shown below.

Column 51, line 26, please delete "FIG. 11" and insert therein --Figures 11A-11B--.

Column 51, line 36, please delete "FIG. 12" and insert therein --Figures 12A-12B--.

Column 51, line 46, please delete "FIG. 13" and insert therein --Figures 13A-13B--.

Column 51, line 58, please delete "FIG. 14" and insert therein --Figures 14A-14B--.

Column 51, line 64, please delete "G283C" and insert therein --G238C--.

Signed and Sealed this

Seventh Day of March, 2000

Attest:

Q. TODD DICKINSON

Attesting Officer

Commissioner of Patents and Trademarks

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
( A ) LENGTH: 840 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS ( B ) LOCATION: 66..800

( x i ) SEQUENCE DESCRIPTION: SEQ ID NO:1:

```
CGGCAACCAG CTGTAAGCGA GGCACGGAAG ACATATGCTT GTGAGACAAA GGTGTCTCTG        60

AAACT ATG GAT GGT ACA AGA ACT TCA CTT GAC ATT GAA GAG TAC TCG           107
      Met Asp Gly Thr Arg Thr Ser Leu Asp Ile Glu Glu Tyr Ser
      1               5                   10

GAT ACT GAG GTA CAG AAA AAC CAA GTA CTA ACT CTG GAA GAA TGG CAA         155
Asp Thr Glu Val Gln Lys Asn Gln Val Leu Thr Leu Glu Glu Trp Gln
15                  20                  25                  30

GAC AAG TGG GTG AAC GGC AAG ACT GCT TTT CAT CAG GAA CAA GGA CAT         203
Asp Lys Trp Val Asn Gly Lys Thr Ala Phe His Gln Glu Gln Gly His
                35                  40                  45

CAG CTA TTA AAG AAG CAT TTA GAT ACT TTC CTT AAA GGC AAG AGT GGA         251
Gln Leu Leu Lys Lys His Leu Asp Thr Phe Leu Lys Gly Lys Ser Gly
        50                  55                  60

CTG AGG GTA TTT TTT CCT CTT TGC GGA AAA GCG GTT GAG ATG AAA TGG         299
Leu Arg Val Phe Phe Pro Leu Cys Gly Lys Ala Val Glu Met Lys Trp
    65                  70                  75

TTT CCA GAC CGG GGA CAC AGT GTA GTT GGT GTG GAA ATC AGT GAA CTT         347
Phe Pro Asp Arg Gly His Ser Val Val Gly Val Glu Ile Ser Glu Leu
80                  85                  90

GGG ATA CAA GAA TTT TTT ACA GAG CAG AAT CTT TCT TAC TCA GAA GAA         395
Gly Ile Gln Glu Phe Phe Thr Glu Gln Asn Leu Ser Tyr Ser Glu Glu
95                  100                 105                 110

CCA ATC ACC GAA ATT CCT GGA ACC AAA GTA TTT AAG AGT TCT TCG GGG         443
Pro Ile Thr Glu Ile Pro Gly Thr Lys Val Phe Lys Ser Ser Ser Gly
                115                 120                 125

AAC ATT TCA TTG TAC TGT TGC AGT ATT TTT GAT CTT CCC AGG ACA AAT         491
Asn Ile Ser Leu Tyr Cys Cys Ser Ile Phe Asp Leu Pro Arg Thr Asn
        130                 135                 140

ATT GGC AAA TTT GAC ATG ATT TGG GAT AGA GGA GCA TTA GTT GCC ATT         539
Ile Gly Lys Phe Asp Met Ile Trp Asp Arg Gly Ala Leu Val Ala Ile
    145                 150                 155

AAT CCA GGT GAT CGC AAA TGC TAT GCA GAT ACA ATG TTT TCC CTC CTG         587
Asn Pro Gly Asp Arg Lys Cys Tyr Ala Asp Thr Met Phe Ser Leu Leu
160                 165                 170

GGA AAG AAG TTT CAG TAT CTC CTG TGT GTT CTT TCT TAT GAT CCA ACT         635
Gly Lys Lys Phe Gln Tyr Leu Leu Cys Val Leu Ser Tyr Asp Pro Thr
175                 180                 185                 190

AAA CAT CCA GGT CCA CCA TTT TAT GTT CCA CAT GCT GAA ATT GAA AGG         683
Lys His Pro Gly Pro Pro Phe Tyr Val Pro His Ala Glu Ile Glu Arg
                195                 200                 205

TTG TTT GGT AAA ATA TGC AAT ATA CGT TGT CTT GAG AAG GTT GAT GCT         731
Leu Phe Gly Lys Ile Cys Asn Ile Arg Cys Leu Glu Lys Val Asp Ala
        210                 215                 220

TTT GAA GAA CGA CAT AAA AGT TGG GGA ATT GAC TGT CTT TTT GAA AAG         779
Phe Glu Glu Arg His Lys Ser Trp Gly Ile Asp Cys Leu Phe Glu Lys
    225                 230                 235

TTA TAT CTA CTT ACA GAA AAG TAAATGAGAC ATAGATAAAA TAAAATCACA            830
Leu Tyr Leu Leu Thr Glu Lys
240                 245

CTGACATGTT                                                               840
```

( 2 ) INFORMATION FOR SEQ ID NO:2:

( i ) SEQUENCE CHARACTERISTICS:
        ( A ) LENGTH: 245 amino acids
        ( B ) TYPE: amino acid
        ( D ) TOPOLOGY: linear (ii) MOLECULE TYPE: protein (xi) SEQUENCE DESCRIPTION: SEQ ID NO:2:

| Met | Asp | Gly | Thr | Arg | Thr | Ser | Leu | Asp | Ile | Glu | Glu | Tyr | Ser | Asp | Thr |
|---|---|---|---|---|---|---|---|---|---|---|---|---|---|---|---|
| 1 | | | | 5 | | | | | 10 | | | | | 15 | |

| Glu | Val | Gln | Lys | Asn | Gln | Val | Leu | Thr | Leu | Glu | Glu | Trp | Gln | Asp | Lys |
|---|---|---|---|---|---|---|---|---|---|---|---|---|---|---|---|
| | | | 20 | | | | | 25 | | | | | 30 | | |

| Trp | Val | Asn | Gly | Lys | Thr | Ala | Phe | His | Gln | Glu | Gln | Gly | His | Gln | Leu |
|---|---|---|---|---|---|---|---|---|---|---|---|---|---|---|---|
| | | | 35 | | | | | 40 | | | | | 45 | | |

| Leu | Lys | Lys | His | Leu | Asp | Thr | Phe | Leu | Lys | Gly | Lys | Ser | Gly | Leu | Arg |
|---|---|---|---|---|---|---|---|---|---|---|---|---|---|---|---|
| | 50 | | | | | 55 | | | | | 60 | | | | |

| Val | Phe | Phe | Pro | Leu | Cys | Gly | Lys | Ala | Val | Glu | Met | Lys | Trp | Phe | Pro |
|---|---|---|---|---|---|---|---|---|---|---|---|---|---|---|---|
| 65 | | | | | 70 | | | | | 75 | | | | | 80 |

| Asp | Arg | Gly | His | Ser | Val | Val | Gly | Val | Glu | Ile | Ser | Glu | Leu | Gly | Ile |
|---|---|---|---|---|---|---|---|---|---|---|---|---|---|---|---|
| | | | | 85 | | | | | 90 | | | | | 95 | |

| Gln | Glu | Phe | Phe | Thr | Glu | Gln | Asn | Leu | Ser | Tyr | Ser | Glu | Glu | Pro | Ile |
|---|---|---|---|---|---|---|---|---|---|---|---|---|---|---|---|
| | | | 100 | | | | | 105 | | | | | 110 | | |

| Thr | Glu | Ile | Pro | Gly | Thr | Lys | Val | Phe | Lys | Ser | Ser | Ser | Gly | Asn | Ile |
|---|---|---|---|---|---|---|---|---|---|---|---|---|---|---|---|
| | | | 115 | | | | | 120 | | | | | 125 | | |

| Ser | Leu | Tyr | Cys | Cys | Ser | Ile | Phe | Asp | Leu | Pro | Arg | Thr | Asn | Ile | Gly |
|---|---|---|---|---|---|---|---|---|---|---|---|---|---|---|---|
| | 130 | | | | | 135 | | | | | 140 | | | | |

| Lys | Phe | Asp | Met | Ile | Trp | Asp | Arg | Gly | Ala | Leu | Val | Ala | Ile | Asn | Pro |
|---|---|---|---|---|---|---|---|---|---|---|---|---|---|---|---|
| 145 | | | | | 150 | | | | | 155 | | | | | 160 |

| Gly | Asp | Arg | Lys | Cys | Tyr | Ala | Asp | Thr | Met | Phe | Ser | Leu | Leu | Gly | Lys |
|---|---|---|---|---|---|---|---|---|---|---|---|---|---|---|---|
| | | | | 165 | | | | | 170 | | | | | 175 | |

| Lys | Phe | Gln | Tyr | Leu | Leu | Cys | Val | Leu | Ser | Tyr | Asp | Pro | Thr | Lys | His |
|---|---|---|---|---|---|---|---|---|---|---|---|---|---|---|---|
| | | | 180 | | | | | 185 | | | | | 190 | | |

| Pro | Gly | Pro | Pro | Phe | Tyr | Val | Pro | His | Ala | Glu | Ile | Glu | Arg | Leu | Phe |
|---|---|---|---|---|---|---|---|---|---|---|---|---|---|---|---|
| | | 195 | | | | | 200 | | | | | 205 | | | |

| Gly | Lys | Ile | Cys | Asn | Ile | Arg | Cys | Leu | Glu | Lys | Val | Asp | Ala | Phe | Glu |
|---|---|---|---|---|---|---|---|---|---|---|---|---|---|---|---|
| | 210 | | | | | 215 | | | | | 220 | | | | |

| Glu | Arg | His | Lys | Ser | Trp | Gly | Ile | Asp | Cys | Leu | Phe | Glu | Lys | Leu | Tyr |
|---|---|---|---|---|---|---|---|---|---|---|---|---|---|---|---|
| 225 | | | | | 230 | | | | | 235 | | | | | 240 |

| Leu | Leu | Thr | Glu | Lys |
|---|---|---|---|---|
| | | | | 245 |

(2) INFORMATION FOR SEQ ID NO:3:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 66..800

(xi) SEQUENCE DESCRIPTION: SEQ ID NO:3:

```
CGGCAACCAG CTGTAAGCGA GGCACGGAAG ACATATGCTT GTGAGACAAA GGTGTCTCTG          60

AAACT ATG GAT GGT ACA AGA ACT TCA CTT GAC ATT GAA GAG TAC TCG            107
      Met Asp Gly Thr Arg Thr Ser Leu Asp Ile Glu Glu Tyr Ser
        1               5                  10

GAT ACT GAG GTA CAG AAA AAC CAA GTA CTA ACT CTG GAA GAA TGG CAA          155
Asp Thr Glu Val Gln Lys Asn Gln Val Leu Thr Leu Glu Glu Trp Gln
 15                  20                  25                  30

GAC AAG TGG GTG AAC GGC AAG ACT GCT TTT CAT CAG GAA CAA GGA CAT          203
```

|  |  |  |  |  |  |  |  |  |  |  |  |  |  |  |  |  |
|---|---|---|---|---|---|---|---|---|---|---|---|---|---|---|---|---|
| Asp | Lys | Trp | Val | Asn<br>35 | Gly | Lys | Thr | Ala | Phe<br>40 | His | Gln | Glu | Gln | Gly<br>45 | His |  |
| CAG<br>Gln | CTA<br>Leu | TTA<br>Leu | AAG<br>Lys<br>50 | AAG<br>Lys | CAT<br>His | TTA<br>Leu | GAT<br>Asp | ACT<br>Thr<br>55 | TTC<br>Phe | CTT<br>Leu | AAA<br>Lys | GGC<br>Gly | AAG<br>Lys<br>60 | AGT<br>Ser | GGA<br>Gly | 251 |
| CTG<br>Leu | AGG<br>Arg | GTA<br>Val<br>65 | TTT<br>Phe | TTT<br>Phe | CCT<br>Pro | CTT<br>Leu | TGC<br>Cys<br>70 | GGA<br>Gly | AAA<br>Lys | GCG<br>Ala | GTT<br>Val | GAG<br>Glu<br>75 | ATG<br>Met | AAA<br>Lys | TGG<br>Trp | 299 |
| TTT<br>Phe | GCA<br>Ala<br>80 | GAC<br>Asp | CGG<br>Arg | GGA<br>Gly | CAC<br>His | AGT<br>Ser<br>85 | GTA<br>Val | GTT<br>Val | GGT<br>Gly | GTG<br>Val | GAA<br>Glu<br>90 | ATC<br>Ile | AGT<br>Ser | GAA<br>Glu | CTT<br>Leu | 347 |
| GGG<br>Gly<br>95 | ATA<br>Ile | CAA<br>Gln | GAA<br>Glu | TTT<br>Phe | TTT<br>Phe<br>100 | ACA<br>Thr | GAG<br>Glu | CAG<br>Gln | AAT<br>Asn | CTT<br>Leu<br>105 | TCT<br>Ser | TAC<br>Tyr | TCA<br>Ser | GAA<br>Glu | GAA<br>Glu<br>110 | 395 |
| CCA<br>Pro | ATC<br>Ile | ACC<br>Thr | GAA<br>Glu | ATT<br>Ile<br>115 | CCT<br>Pro | GGA<br>Gly | ACC<br>Thr | AAA<br>Lys | GTA<br>Val<br>120 | TTT<br>Phe | AAG<br>Lys | AGT<br>Ser | TCT<br>Ser | TCG<br>Ser<br>125 | GGG<br>Gly | 443 |
| AAC<br>Asn | ATT<br>Ile | TCA<br>Ser | TTG<br>Leu<br>130 | TAC<br>Tyr | TGT<br>Cys | TGC<br>Cys | AGT<br>Ser | ATT<br>Ile<br>135 | TTT<br>Phe | GAT<br>Asp | CTT<br>Leu | CCC<br>Pro | AGG<br>Arg<br>140 | ACA<br>Thr | AAT<br>Asn | 491 |
| ATT<br>Ile | GGC<br>Gly | AAA<br>Lys<br>145 | TTT<br>Phe | GAC<br>Asp | ATG<br>Met | ATT<br>Ile | TGG<br>Trp<br>150 | GAT<br>Asp | AGA<br>Arg | GGA<br>Gly | ACA<br>Thr | TTA<br>Leu<br>155 | GTT<br>Val | GCC<br>Ala | ATT<br>Ile | 539 |
| AAT<br>Asn | CCA<br>Pro<br>160 | GGT<br>Gly | GAT<br>Asp | CGC<br>Arg | AAA<br>Lys | TGC<br>Cys<br>165 | TAT<br>Tyr | GCA<br>Ala | GAT<br>Asp | ACA<br>Thr | ATG<br>Met<br>170 | TTT<br>Phe | TCC<br>Ser | CTC<br>Leu | CTG<br>Leu | 587 |
| GGA<br>Gly<br>175 | AAG<br>Lys | AAG<br>Lys | TTT<br>Phe | CAG<br>Gln<br>180 | TAT<br>Tyr | CTC<br>Leu | CTG<br>Leu | TGT<br>Cys | GTT<br>Val<br>185 | CTT<br>Leu | TCT<br>Ser | TAT<br>Tyr | GAT<br>Asp | CCA<br>Pro<br>190 | ACT<br>Thr | 635 |
| AAA<br>Lys | CAT<br>His | CCA<br>Pro | GGT<br>Gly | CCA<br>Pro<br>195 | CCA<br>Pro | TTT<br>Phe | TAT<br>Tyr | GTT<br>Val | CCA<br>Pro<br>200 | CAT<br>His | GCT<br>Ala | GAA<br>Glu | ATT<br>Ile | GAA<br>Glu<br>205 | AGG<br>Arg | 683 |
| TTG<br>Leu | TTT<br>Phe | GGT<br>Gly | AAA<br>Lys<br>210 | ATA<br>Ile | TGC<br>Cys | AAT<br>Asn | ATA<br>Ile | CGT<br>Arg<br>215 | TGT<br>Cys | CTT<br>Leu | GAG<br>Glu | AAG<br>Lys | GTT<br>Val<br>220 | GAT<br>Asp | GCT<br>Ala | 731 |
| TTT<br>Phe | GAA<br>Glu | GAA<br>Glu<br>225 | CGA<br>Arg | CAT<br>His | AAA<br>Lys | AGT<br>Ser | TGG<br>Trp<br>230 | GGA<br>Gly | ATT<br>Ile | GAC<br>Asp | TGT<br>Cys | CTT<br>Leu<br>235 | TTT<br>Phe | GAA<br>Glu | AAG<br>Lys | 779 |
| TTA<br>Leu | TAT<br>Tyr<br>240 | CTA<br>Leu | CTT<br>Leu | ACA<br>Thr | GAA<br>Glu | AAG<br>Lys<br>245 | TAAATGAGAC | ATAGATAAAA | TAAAATCACA |  |  |  |  |  |  | 830 |

CTGACATGTT 840

(2) INFORMATION FOR SEQ ID NO:4:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO:4:

|  |  |  |  |  |  |  |  |  |  |  |  |  |  |  |  |
|---|---|---|---|---|---|---|---|---|---|---|---|---|---|---|---|
| Met<br>1 | Asp | Gly | Thr | Arg<br>5 | Thr | Ser | Leu | Asp | Ile<br>10 | Glu | Glu | Tyr | Ser | Asp<br>15 | Thr |
| Glu | Val | Gln | Lys<br>20 | Asn | Gln | Val | Leu | Thr<br>25 | Leu | Glu | Glu | Trp | Gln<br>30 | Asp | Lys |
| Trp | Val | Asn<br>35 | Gly | Lys | Thr | Ala | Phe<br>40 | His | Gln | Glu | Gln | Gly<br>45 | His | Gln | Leu |
| Leu | Lys<br>50 | Lys | His | Leu | Asp | Thr<br>55 | Phe | Leu | Lys | Gly | Lys<br>60 | Ser | Gly | Leu | Arg |

```
Val  Phe  Phe  Pro  Leu  Cys  Gly  Lys  Ala  Val  Glu  Met  Lys  Trp  Phe  Ala
65                  70                       75                       80

Asp  Arg  Gly  His  Ser  Val  Val  Gly  Val  Glu  Ile  Ser  Glu  Leu  Gly  Ile
                    85                       90                       95

Gln  Glu  Phe  Phe  Thr  Glu  Gln  Asn  Leu  Ser  Tyr  Ser  Glu  Pro  Ile
               100                 105                      110

Thr  Glu  Ile  Pro  Gly  Thr  Lys  Val  Phe  Lys  Ser  Ser  Gly  Asn  Ile
               115                 120                      125

Ser  Leu  Tyr  Cys  Cys  Ser  Ile  Phe  Asp  Leu  Pro  Arg  Thr  Asn  Ile  Gly
          130                 135                 140

Lys  Phe  Asp  Met  Ile  Trp  Asp  Arg  Gly  Thr  Leu  Val  Ala  Ile  Asn  Pro
145                      150                 155                           160

Gly  Asp  Arg  Lys  Cys  Tyr  Ala  Asp  Thr  Met  Phe  Ser  Leu  Leu  Gly  Lys
                    165                      170                      175

Lys  Phe  Gln  Tyr  Leu  Leu  Cys  Val  Leu  Ser  Tyr  Asp  Pro  Thr  Lys  His
               180                 185                      190

Pro  Gly  Pro  Pro  Phe  Tyr  Val  Pro  His  Ala  Glu  Ile  Glu  Arg  Leu  Phe
               195                 200                      205

Gly  Lys  Ile  Cys  Asn  Ile  Arg  Cys  Leu  Glu  Lys  Val  Asp  Ala  Phe  Glu
          210                 215                 220

Glu  Arg  His  Lys  Ser  Trp  Gly  Ile  Asp  Cys  Leu  Phe  Glu  Lys  Leu  Tyr
225                      230                      235                      240

Leu  Leu  Thr  Glu  Lys
               245
```

( 2 ) INFORMATION FOR SEQ ID NO:5:

( i ) SEQUENCE CHARACTERISTICS:
        ( A ) LENGTH: 840 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 66..800

( x i ) SEQUENCE DESCRIPTION: SEQ ID NO:5:

```
CGGCAACCAG  CTGTAAGCGA  GGCACGGAAG  ACATATGCTT  GTGAGACAAA  GGTGTCTCTG                    60

AAACT ATG GAT GGT ACA AGA ACT TCA CTT GAC ATT GAA GAG TAC TCG                           107
      Met Asp Gly Thr Arg Thr Ser Leu Asp Ile Glu Glu Tyr Ser
      1               5                   10

GAT ACT GAG GTA CAG AAA AAC CAA GTA CTA ACT CTG GAA GAA TGG CAA                         155
Asp Thr Glu Val Gln Lys Asn Gln Val Leu Thr Leu Glu Glu Trp Gln
15                  20                  25                  30

GAC AAG TGG GTG AAC GGC AAG ACT GCT TTT CAT CAG GAA CAA GGA CAT                         203
Asp Lys Trp Val Asn Gly Lys Thr Ala Phe His Gln Glu Gln Gly His
                35                  40                  45

CAG CTA TTA AAG AAG CAT TTA GAT ACT TTC CTT AAA GGC AAG AGT GGA                         251
Gln Leu Leu Lys Lys His Leu Asp Thr Phe Leu Lys Gly Lys Ser Gly
            50                  55                  60

CTG AGG GTA TTT TTT CCT CTT TGC GGA AAA GCG GTT GAG ATG AAA TGG                         299
Leu Arg Val Phe Phe Pro Leu Cys Gly Lys Ala Val Glu Met Lys Trp
        65                  70                  75

TTT GCA GAC CGG GGA CAC AGT GTA GTT GGT GTG GAA ATC AGT GAA CTT                         347
Phe Ala Asp Arg Gly His Ser Val Val Gly Val Glu Ile Ser Glu Leu
    80                  85                  90
```

| | | | | | | | | | | | | | | | | |
|---|---|---|---|---|---|---|---|---|---|---|---|---|---|---|---|---|
|GGG|ATA|CAA|GAA|TTT|TTT|ACA|GAG|CAG|AAT|CTT|TCT|TAC|TCA|GAA|GAA|395|
|Gly|Ile|Gln|Glu|Phe|Phe|Thr|Glu|Gln|Asn|Leu|Ser|Tyr|Ser|Glu|Glu| |
|95| | | |100| | | | |105| | | | |110| | |
|CCA|ATC|ACC|GAA|ATT|CCT|GGA|ACC|AAA|GTA|TTT|AAG|AGT|TCT|TCG|GGG|443|
|Pro|Ile|Thr|Glu|Ile|Pro|Gly|Thr|Lys|Val|Phe|Lys|Ser|Ser|Ser|Gly| |
| | | | |115| | | |120| | | | |125| | | |
|AAC|ATT|TCA|TTG|TAC|TGT|TGC|AGT|ATT|TTT|GAT|CTT|CCC|AGG|ACA|AAT|491|
|Asn|Ile|Ser|Leu|Tyr|Cys|Cys|Ser|Ile|Phe|Asp|Leu|Pro|Arg|Thr|Asn| |
| | |130| | | | |135| | | | |140| | | | |
|ATT|GGC|AAA|TTT|GAC|ATG|ATT|TGG|GAT|AGA|GGA|GCA|TTA|GTT|GCC|ATT|539|
|Ile|Gly|Lys|Phe|Asp|Met|Ile|Trp|Asp|Arg|Gly|Ala|Leu|Val|Ala|Ile| |
| | |145| | | | |150| | | | |155| | | | |
|AAT|CCA|GGT|GAT|CGC|AAA|TGC|TAT|GCA|GAT|ACA|ATG|TTT|TCC|CTC|CTG|587|
|Asn|Pro|Gly|Asp|Arg|Lys|Cys|Tyr|Ala|Asp|Thr|Met|Phe|Ser|Leu|Leu| |
| |160| | | | |165| | | | |170| | | | | |
|GGA|AAG|AAG|TTT|CAG|TAT|CTC|CTG|TGT|GTT|CTT|TCT|TAT|GAT|CCA|ACT|635|
|Gly|Lys|Lys|Phe|Gln|Tyr|Leu|Leu|Cys|Val|Leu|Ser|Tyr|Asp|Pro|Thr| |
|175| | | |180| | | | |185| | | | |190| | |
|AAA|CAT|CCA|GGT|CCA|CCA|TTT|TAT|GTT|CCA|CAT|GCT|GAA|ATT|GAA|AGG|683|
|Lys|His|Pro|Gly|Pro|Pro|Phe|Tyr|Val|Pro|His|Ala|Glu|Ile|Glu|Arg| |
| | | |195| | | | |200| | | | |205| | | |
|TTG|TTT|GGT|AAA|ATA|TGC|AAT|ATA|CGT|TGT|CTT|GAG|AAG|GTT|GAT|GCT|731|
|Leu|Phe|Gly|Lys|Ile|Cys|Asn|Ile|Arg|Cys|Leu|Glu|Lys|Val|Asp|Ala| |
| | |210| | | | |215| | | | |220| | | | |
|TTT|GAA|GAA|CGA|CAT|AAA|AGT|TGG|GGA|ATT|GAC|TGT|CTT|TTT|GAA|AAG|779|
|Phe|Glu|Glu|Arg|His|Lys|Ser|Trp|Gly|Ile|Asp|Cys|Leu|Phe|Glu|Lys| |
| | |225| | | | |230| | | | |235| | | | |
|TTA|TGT|CTA|CTT|ACA|GAA|AAG|TAAATGAGAC|ATAGATAAAA|TAAAATCACA| | | | | | |830|
|Leu|Cys|Leu|Leu|Thr|Glu|Lys| | | | | | | | | | |
| |240| | | | |245| | | | | | | | | | |
|CTGACATGTT| | | | | | | | | | | | | | | |840|

( 2 ) INFORMATION FOR SEQ ID NO:6:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
|Met|Asp|Gly|Thr|Arg|Thr|Ser|Leu|Asp|Ile|Glu|Glu|Tyr|Ser|Asp|Thr|
|1| | | |5| | | | |10| | | | |15| |
|Glu|Val|Gln|Lys|Asn|Gln|Val|Leu|Thr|Leu|Glu|Glu|Trp|Gln|Asp|Lys|
| | | |20| | | | |25| | | | |30| | |
|Trp|Val|Asn|Gly|Lys|Thr|Ala|Phe|His|Gln|Glu|Gln|Gly|His|Gln|Leu|
| | |35| | | | |40| | | | |45| | | |
|Leu|Lys|Lys|His|Leu|Asp|Thr|Phe|Leu|Lys|Gly|Lys|Ser|Gly|Leu|Arg|
| |50| | | | |55| | | | |60| | | | |
|Val|Phe|Phe|Pro|Leu|Cys|Gly|Lys|Ala|Val|Glu|Met|Lys|Trp|Phe|Ala|
|65| | | | |70| | | | |75| | | | |80|
|Asp|Arg|Gly|His|Ser|Val|Val|Gly|Val|Glu|Ile|Ser|Glu|Leu|Gly|Ile|
| | | | |85| | | | |90| | | | |95| |
|Gln|Glu|Phe|Phe|Thr|Glu|Gln|Asn|Leu|Ser|Tyr|Ser|Glu|Glu|Pro|Ile|
| | | |100| | | | |105| | | | |110| | |
|Thr|Glu|Ile|Pro|Gly|Thr|Lys|Val|Phe|Lys|Ser|Ser|Ser|Gly|Asn|Ile|
| | |115| | | | |120| | | | |125| | | |
|Ser|Leu|Tyr|Cys|Cys|Ser|Ile|Phe|Asp|Leu|Pro|Arg|Thr|Asn|Ile|Gly|
| |130| | | | |135| | | | |140| | | | |

```
Lys  Phe  Asp  Met  Ile  Trp  Asp  Arg  Gly  Ala  Leu  Val  Ala  Ile  Asn  Pro
145                      150                      155                      160

Gly  Asp  Arg  Lys  Cys  Tyr  Ala  Asp  Thr  Met  Phe  Ser  Leu  Leu  Gly  Lys
                    165                      170                      175

Lys  Phe  Gln  Tyr  Leu  Leu  Cys  Val  Leu  Ser  Tyr  Asp  Pro  Thr  Lys  His
                180                      185                      190

Pro  Gly  Pro  Pro  Phe  Tyr  Val  Pro  His  Ala  Glu  Ile  Glu  Arg  Leu  Phe
          195                      200                      205

Gly  Lys  Ile  Cys  Asn  Ile  Arg  Cys  Leu  Glu  Lys  Val  Asp  Ala  Phe  Glu
     210                      215                      220

Glu  Arg  His  Lys  Ser  Trp  Gly  Ile  Asp  Cys  Leu  Phe  Glu  Lys  Leu  Cys
225                      230                      235                      240

Leu  Leu  Thr  Glu  Lys
               245
```

( 2 ) INFORMATION FOR SEQ ID NO:7:

( i ) SEQUENCE CHARACTERISTICS:
        ( A ) LENGTH: 840 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 66..800

( x i ) SEQUENCE DESCRIPTION: SEQ ID NO:7:

```
CGGCAACCAG  CTGTAAGCGA  GGCACGGAAG  ACATATGCTT  GTGAGACAAA  GGTGTCTCTG              60

AAACT ATG GAT GGT ACA AGA ACT TCA CTT GAC ATT GAA GAG TAC TCG                     107
      Met Asp Gly Thr Arg Thr Ser Leu Asp Ile Glu Glu Tyr Ser
       1           5                          10

GAT ACT GAG GTA CAG AAA AAC CAA GTA CTA ACT CTG GAA GAA TGG CAA                   155
Asp Thr Glu Val Gln Lys Asn Gln Val Leu Thr Leu Glu Glu Trp Gln
 15              20                  25                      30

GAC AAG TGG GTG AAC GGC AAG ACT GCT TTT CAT CAG GAA CAA GGA CAT                   203
Asp Lys Trp Val Asn Gly Lys Thr Ala Phe His Gln Glu Gln Gly His
                 35                  40                  45

CAG CTA TTA AAG AAG CAT TTA GAT ACT TTC CTT AAA GGC AAG AGT GGA                   251
Gln Leu Leu Lys Lys His Leu Asp Thr Phe Leu Lys Gly Lys Ser Gly
             50                  55                  60

CTG AGG GTA TTT TTT CCT CTT TGC GGA AAA GCG GTT GAG ATG AAA TGG                   299
Leu Arg Val Phe Phe Pro Leu Cys Gly Lys Ala Val Glu Met Lys Trp
         65                  70                  75

TTT GCA GAC CGG GGA CAC AGT GTA GTT GGT GTG GAA ATC AGT GAA CTT                   347
Phe Ala Asp Arg Gly His Ser Val Val Gly Val Glu Ile Ser Glu Leu
     80                  85                  90

GGG ATA CAA GAA TTT TTT ACA GAG CAG AAT CTT TCT TAC TCA GAA GAA                   395
Gly Ile Gln Glu Phe Phe Thr Glu Gln Asn Leu Ser Tyr Ser Glu Glu
 95                  100                 105                 110

CCA ATC ACC GAA ATT CCT GGA ACC AAA GTA TTT AAG AGT TCT TCG GGG                   443
Pro Ile Thr Glu Ile Pro Gly Thr Lys Val Phe Lys Ser Ser Ser Gly
                 115                 120                 125

AAC ATT TCA TTG TAC TGT TGC AGT ATT TTT GAT CTT CCC AGG ACA AAT                   491
Asn Ile Ser Leu Tyr Cys Cys Ser Ile Phe Asp Leu Pro Arg Thr Asn
             130                 135                 140

ATT GGC AAA TTT GAC ATG ATT TGG GAT AGA GGA ACA TTA GTT GCC ATT                   539
Ile Gly Lys Phe Asp Met Ile Trp Asp Arg Gly Thr Leu Val Ala Ile
         145                 150                 155
```

|  |  |  |  |  |  |  |  |  |  |  |  |  |  |  |  |
|---|---|---|---|---|---|---|---|---|---|---|---|---|---|---|---|
| AAT | CCA | GGT | GAT | CGC | AAA | TGC | TAT | GCA | GAT | ACA | ATG | TTT | TCC | CTC | CTG | 587
| Asn | Pro | Gly | Asp | Arg | Lys | Cys | Tyr | Ala | Asp | Thr | Met | Phe | Ser | Leu | Leu |
| 160 |  |  |  |  | 165 |  |  |  |  | 170 |  |  |  |  |  |
| GGA | AAG | AAG | TTT | CAG | TAT | CTC | CTG | TGT | GTT | CTT | TCT | TAT | GAT | CCA | ACT | 635
| Gly | Lys | Lys | Phe | Gln | Tyr | Leu | Leu | Cys | Val | Leu | Ser | Tyr | Asp | Pro | Thr |
| 175 |  |  |  |  | 180 |  |  |  |  | 185 |  |  |  |  | 190 |
| AAA | CAT | CCA | GGT | CCA | CCA | TTT | TAT | GTT | CCA | CAT | GCT | GAA | ATT | GAA | AGG | 683
| Lys | His | Pro | Gly | Pro | Pro | Phe | Tyr | Val | Pro | His | Ala | Glu | Ile | Glu | Arg |
|  |  |  | 195 |  |  |  |  |  | 200 |  |  |  |  | 205 |  |
| TTG | TTT | GGT | AAA | ATA | TGC | AAT | ATA | CGT | TGT | CTT | GAG | AAG | GTT | GAT | GCT | 731
| Leu | Phe | Gly | Lys | Ile | Cys | Asn | Ile | Arg | Cys | Leu | Glu | Lys | Val | Asp | Ala |
|  |  |  | 210 |  |  |  |  | 215 |  |  |  |  | 220 |  |  |
| TTT | GAA | GAA | CGA | CAT | AAA | AGT | TGG | GGA | ATT | GAC | TGT | CTT | TTT | GAA | AAG | 779
| Phe | Glu | Glu | Arg | His | Lys | Ser | Trp | Gly | Ile | Asp | Cys | Leu | Phe | Glu | Lys |
|  |  | 225 |  |  |  |  | 230 |  |  |  |  | 235 |  |  |  |
| TTA | TGT | CTA | CTT | ACA | GAA | AAG | TAAATGAGAC | ATAGATAAAA | TAAAATCACA |  |  |  |  |  |  | 830
| Leu | Cys | Leu | Leu | Thr | Glu | Lys |  |  |  |  |  |  |  |  |  |
| 240 |  |  |  |  | 245 |  |  |  |  |  |  |  |  |  |  |

CTGACATGTT                                                                                                                                          840

( 2 ) INFORMATION FOR SEQ ID NO:8:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Asp | Gly | Thr | Arg | Thr | Ser | Leu | Asp | Ile | Glu | Glu | Tyr | Ser | Asp | Thr |
|---|---|---|---|---|---|---|---|---|---|---|---|---|---|---|---|
| 1 |  |  |  | 5 |  |  |  |  | 10 |  |  |  |  | 15 |  |
| Glu | Val | Gln | Lys | Asn | Gln | Val | Leu | Thr | Leu | Glu | Glu | Trp | Gln | Asp | Lys |
|  |  |  | 20 |  |  |  |  | 25 |  |  |  |  | 30 |  |  |
| Trp | Val | Asn | Gly | Lys | Thr | Ala | Phe | His | Gln | Glu | Gln | Gly | His | Gln | Leu |
|  |  | 35 |  |  |  |  | 40 |  |  |  |  | 45 |  |  |  |
| Leu | Lys | Lys | His | Leu | Asp | Thr | Phe | Leu | Lys | Gly | Lys | Ser | Gly | Leu | Arg |
| 50 |  |  |  |  | 55 |  |  |  |  | 60 |  |  |  |  |  |
| Val | Phe | Phe | Pro | Leu | Cys | Gly | Lys | Ala | Val | Glu | Met | Lys | Trp | Phe | Ala |
| 65 |  |  |  |  | 70 |  |  |  |  | 75 |  |  |  |  | 80 |
| Asp | Arg | Gly | His | Ser | Val | Val | Gly | Val | Glu | Ile | Ser | Glu | Leu | Gly | Ile |
|  |  |  |  | 85 |  |  |  |  | 90 |  |  |  |  | 95 |  |
| Gln | Glu | Phe | Phe | Thr | Glu | Gln | Asn | Leu | Ser | Tyr | Ser | Glu | Glu | Pro | Ile |
|  |  |  | 100 |  |  |  |  | 105 |  |  |  |  | 110 |  |  |
| Thr | Glu | Ile | Pro | Gly | Thr | Lys | Val | Phe | Lys | Ser | Ser | Gly | Asn | Ile |  |
|  |  | 115 |  |  |  |  | 120 |  |  |  |  | 125 |  |  |  |
| Ser | Leu | Tyr | Cys | Cys | Ser | Ile | Phe | Asp | Leu | Pro | Arg | Thr | Asn | Ile | Gly |
|  | 130 |  |  |  |  | 135 |  |  |  |  | 140 |  |  |  |  |
| Lys | Phe | Asp | Met | Ile | Trp | Asp | Arg | Gly | Thr | Leu | Val | Ala | Ile | Asn | Pro |
| 145 |  |  |  |  | 150 |  |  |  |  | 155 |  |  |  |  | 160 |
| Gly | Asp | Arg | Lys | Cys | Tyr | Ala | Asp | Thr | Met | Phe | Ser | Leu | Leu | Gly | Lys |
|  |  |  |  | 165 |  |  |  |  | 170 |  |  |  |  | 175 |  |
| Lys | Phe | Gln | Tyr | Leu | Leu | Cys | Val | Leu | Ser | Tyr | Asp | Pro | Thr | Lys | His |
|  |  |  | 180 |  |  |  |  | 185 |  |  |  |  | 190 |  |  |
| Pro | Gly | Pro | Pro | Phe | Tyr | Val | Pro | His | Ala | Glu | Ile | Glu | Arg | Leu | Phe |
|  |  | 195 |  |  |  |  | 200 |  |  |  |  | 205 |  |  |  |
| Gly | Lys | Ile | Cys | Asn | Ile | Arg | Cys | Leu | Glu | Lys | Val | Asp | Ala | Phe | Glu |
|  | 210 |  |  |  |  | 215 |  |  |  |  | 220 |  |  |  |  |

```
Glu Arg His Lys Ser Trp Gly Ile Asp Cys Leu Phe Glu Lys Leu Cys
225                 230                 235                 240

Leu Leu Thr Glu Lys
            245
```

( 2 ) INFORMATION FOR SEQ ID NO:9:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GTAGGTTGAA TACTACATCT GCACTTTAAA AAATTTGAAT GCTTGCCAGG CAGTGCAGGC   60
ATGGGAGTGG AGGTGTCTTC CTCACTCTCT TCCTCCTGTG TAACATCCAC AAAGCATTTT  120
TTTGAATGTC TGTTCTGCAG ATATTTTTAT TACACACTCG TCTGCACACT TTAATGTGTT  180
TTGTCTTTGG TTAGCTCCCA AACTATGGGA AACTGAGGCA GCTAGGGAAA AAGAAAGGTG  240
AGTAAGACAG TGTCTTCTAC CTTGCACCTG GGCCTGTAAT AGAAATGAAT TTCAAGTAGC  300
CAAGGGAGAT AAGAGCTCAT CTCCTGAAAG TCCCTGATAC CTGAGCCAGA GGCTGGGGGC  360
AGAGTTGTTG CACACTGTCC TTTGTTCCTT CTTCATGTCC CCAAATCATA ACAGAGTGGG  420
GAGGCTGCTG CCACAGGCTC CTAAAACCAT GAGGGGATGG ACAGCTCTCC ACACCCAGGT  480
CCACACATTC CTCTAGGAGG AAACGCAGAC GTGAGATCCT AATACCTTGA CGATTGTTGA  540
AGTACCAGCA TGCACCATGG GGGACGCTGC TCATCTTCTT AAAGATTTGA TTTTTCTCCC  600
ATAAAATGTT TTTTCTCTTT CTGGTAG                                     627
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
ATAACAGAGT GGGGAGGCTG C                                            21
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
TGGTTTGCAG AC                                                      12
```

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear (i i) MOLECULE TYPE: peptide (v) FRAGMENT TYPE: internal (x i) SEQUENCE DESCRIPTION: SEQ ID NO:12:

Trp Phe Ala Asp
1

(2) INFORMATION FOR SEQ ID NO:13:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

TGGTTTCCAG AC 12

(2) INFORMATION FOR SEQ ID NO:14:

(i) SEQUENCE CHARACTERISTICS:
(A) LENGTH: 4 amino acids
(B) TYPE: amino acid
(C) STRANDEDNESS: Not Relevant
(D) TOPOLOGY: linear (i i) MOLECULE TYPE: peptide (v) FRAGMENT TYPE: internal (x i) SEQUENCE DESCRIPTION: SEQ ID NO:14:

Trp Phe Pro Asp
1

(2) INFORMATION FOR SEQ ID NO:15:

(i) SEQUENCE CHARACTERISTICS:
(A) LENGTH: 12 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:15:

AGAGGAGCAT TA 12

(2) INFORMATION FOR SEQ ID NO:16:

(i) SEQUENCE CHARACTERISTICS:
(A) LENGTH: 4 amino acids
(B) TYPE: amino acid
(C) STRANDEDNESS: Not Relevant
(D) TOPOLOGY: linear (i i) MOLECULE TYPE: peptide (v) FRAGMENT TYPE: internal (x i) SEQUENCE DESCRIPTION: SEQ ID NO:16:

Arg Gly Ala Leu
1

(2) INFORMATION FOR SEQ ID NO:17:

(i) SEQUENCE CHARACTERISTICS:

(A) LENGTH: 12 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:17:

AAGTTATATC TA 12

(2) INFORMATION FOR SEQ ID NO:18:

(i) SEQUENCE CHARACTERISTICS:
(A) LENGTH: 4 amino acids
(B) TYPE: amino acid
(C) STRANDEDNESS: Not Relevant
(D) TOPOLOGY: linear (ii) MOLECULE TYPE: peptide (v) FRAGMENT TYPE: internal (xi) SEQUENCE DESCRIPTION: SEQ ID NO:18:

Lys Leu Tyr Leu
1

(2) INFORMATION FOR SEQ ID NO:19:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

AGAGGAACAT TA 12

(2) INFORMATION FOR SEQ ID NO:20:

(i) SEQUENCE CHARACTERISTICS:
(A) LENGTH: 4 amino acids
(B) TYPE: amino acid
(C) STRANDEDNESS: Not Relevant
(D) TOPOLOGY: linear (ii) MOLECULE TYPE: peptide (v) FRAGMENT TYPE: internal (xi) SEQUENCE DESCRIPTION: SEQ ID NO:20:

Arg Gly Thr Leu
1

(2) INFORMATION FOR SEQ ID NO:21:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:21:

AAGTTATGTC TA 12

(2) INFORMATION FOR SEQ ID NO:22:

( i ) SEQUENCE CHARACTERISTICS:
   ( A ) LENGTH: 4 amino acids
   ( B ) TYPE: amino acid
   ( C ) STRANDEDNESS: Not Relevant
   ( D ) TOPOLOGY: linear ( i i ) MOLECULE TYPE: peptide ( v ) FRAGMENT TYPE: internal ( x i ) SEQUENCE DESCRIPTION: SEQ ID NO:22:

Lys Leu Cys Leu
 1

( 2 ) INFORMATION FOR SEQ ID NO:23:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:23:

GCACATACAC CAAATGTCTG AACCTGCGGT            30

( 2 ) INFORMATION FOR SEQ ID NO:24:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:24:

GGCTTGAAAC CGATAGTCCC TCTAAGAAG             29

( 2 ) INFORMATION FOR SEQ ID NO:25:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:25:

GCACGGAAGA CATATGCTTG TGAGAC                26

( 2 ) INFORMATION FOR SEQ ID NO:26:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:26:

CAGGCTTTAG CATAATTTTC AATTCCTC              28

( 2 ) INFORMATION FOR SEQ ID NO:27:

( i ) SEQUENCE CHARACTERISTICS:
      ( A ) LENGTH: 41 base pairs (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:27:

CGGATCCAAA ATGGATGGTA CAAGAACTTC ACTTGACATT G     41

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:28:

CGGAATTCAG GCTTTAGCAT AATTTTC     27

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:29:

TCAGGAACAA GGACATCAGC     20

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:30:

GGTTCCAGGA ATTTCGGTGA TTG     23

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:31:

GTGTCCCCGG TCTGC     15

(2) INFORMATION FOR SEQ ID NO:32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: cDNA ( x i ) SEQUENCE DESCRIPTION: SEQ ID NO:32:

GTGTCCCCGG TCTGG                                                                                        15

( 2 ) INFORMATION FOR SEQ ID NO:33:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

GCATTTAGAT ACTTTCCTTA AAGGCA                                                                            26

( 2 ) INFORMATION FOR SEQ ID NO:34:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

GGCTTGAAAC CGATAGTCCC TCTAAGAAG                                                                         29

( 2 ) INFORMATION FOR SEQ ID NO:35:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

CGGAATTCTT ACTTTTCTGT AAGTAGATAT AACTTTTC                                                               38

( 2 ) INFORMATION FOR SEQ ID NO:36:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

CGGAATTCTT ACTTTTCTGT AAGTAGACAT AACTTTTC                                                               38

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

CAGAAGAACC AATCACCG                                                                                     18

( 2 ) INFORMATION FOR SEQ ID NO:38:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

ATGTAATACG ACTCACTATA ACCTGGATTA ATGGCAAC        38